United States Patent
Williams et al.

(10) Patent No.: US 9,981,068 B2
(45) Date of Patent: May 29, 2018

(54) POLYMERS WHICH RESIST BACTERIAL ATTACHMENT

(75) Inventors: Paul Williams, Nottingham (GB); Morgan Russell Alexander, Nottingham (GB); Martyn Christopher Davies, Nottingham (GB); Robert Langer, Cambridge, MA (US); Daniel Griffith Anderson, Cambridge, MA (US)

(73) Assignees: The University of Nottingham, Nottingham (GB); Massachusetts Institute of Technology, Cambridge, MA (US)

( * ) Notice: Subject to any disclaimer, the term of this patent is extended or adjusted under 35 U.S.C. 154(b) by 675 days.

(21) Appl. No.: 14/115,451

(22) PCT Filed: May 4, 2012

(86) PCT No.: PCT/GB2012/050987
§ 371 (c)(1),
(2), (4) Date: Jul. 3, 2014

(87) PCT Pub. No.: WO2012/150467
PCT Pub. Date: Nov. 8, 2012

(65) Prior Publication Data
US 2014/0314826 A1    Oct. 23, 2014

(30) Foreign Application Priority Data

May 4, 2011    (GB) .................................. 1107416.8
Jan. 18, 2012   (GB) .................................. 1200832.2

(51) Int. Cl.
*A61L 29/16*    (2006.01)
*A01N 37/12*    (2006.01)
(Continued)

(52) U.S. Cl.
CPC .............. *A61L 29/16* (2013.01); *A01N 37/12* (2013.01); *A01N 37/20* (2013.01); *A61L 27/34* (2013.01);
(Continued)

(58) Field of Classification Search
CPC ........ A61L 29/16; A61L 29/085; A61L 31/14; A61L 31/10; A61L 27/50; A61L 27/34;
(Continued)

(56) References Cited

U.S. PATENT DOCUMENTS

2004/0208983 A1    10/2004  Hill et al.
2010/0285577 A1*   11/2010  Izadyar ................ C12N 5/0609
                                                435/325

FOREIGN PATENT DOCUMENTS

EP          0 852 238 A2    7/1998
WO       WO 00/41738 A1    7/2000
(Continued)

OTHER PUBLICATIONS

Raad et al, Anti-adherence activity and antimicrobial durability of anti-infective-coated catheters against multidrug resistant bacteria, 2008, JAC, 62, pp. 746-750.*

*Primary Examiner* — Trevor Love
(74) *Attorney, Agent, or Firm* — Alston & Bird, LLP

(57) ABSTRACT

The invention provides a method for inhibiting bacterial attachment to a surface, the method comprising forming the surface from a polymer, or applying a polymer to the surface, wherein the polymer is a homopolymer formed from a (meth) acrylate or (meth) acrylamide monomer or a copolymer formed from one or more (meth) acrylate or (meth) acrylamide monomers, wherein the (meth) acrylate or (meth) acrylamide monomers are of formula (I) or (II):

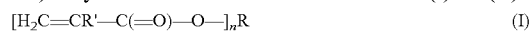

$[H_2C=CR'-C(=O)-O-]_nR$  (I)

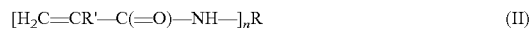

$[H_2C=CR'-C(=O)-NH-]_nR$  (II)

(Continued)

wherein
n is 1, 2 or 3,
R' is independently H or CH$_3$,
R is an organic group having a total of from 2 to 24 carbon atoms, wherein the organic group includes an aliphatic or aromatic hydrocarbon moiety and wherein the organic group does not include any hydroxyl groups.

24 Claims, 18 Drawing Sheets

(51) Int. Cl.
*A01N 37/20* (2006.01)
*A61L 29/08* (2006.01)
*A61L 31/14* (2006.01)
*A61L 31/10* (2006.01)
*A61L 27/50* (2006.01)
*A61L 27/34* (2006.01)
*A61L 29/14* (2006.01)
*C08F 220/56* (2006.01)
*C08F 220/24* (2006.01)
*C08F 220/18* (2006.01)
*C08F 220/22* (2006.01)
*C08F 222/10* (2006.01)

(52) U.S. Cl.
CPC .............. *A61L 27/50* (2013.01); *A61L 29/085* (2013.01); *A61L 29/14* (2013.01); *A61L 31/10* (2013.01); *A61L 31/14* (2013.01); *C08F 220/18* (2013.01); *C08F 220/22* (2013.01); *C08F 220/24* (2013.01); *C08F 220/56* (2013.01); *C08F 222/1006* (2013.01)

(58) Field of Classification Search
CPC ......... A61L 29/14; A01N 37/12; A01N 37/20; C08F 220/56; C08F 220/24; C08F 220/18; C08F 220/22; C08F 222/1006
See application file for complete search history.

(56) References Cited

FOREIGN PATENT DOCUMENTS

| WO | WO 2008/088394 A2 | 7/2008 | |
|----|----|----|----|
| WO | WO 2008/131360 A1 | 10/2008 | |
| WO | WO 2010/074806 A1 | 7/2010 | |
| WO | WO 2010124091 | * 10/2010 | .............. H01J 49/14 |

* cited by examiner

| Ion | Positive coefficient$_{PAO1}$ (x10$^7$) | Positive coefficient $_{8325-4}$ (x10$^7$) | Ion | Negative coefficient$_{PAO1}$ (x10$^7$) | Negative coefficient $_{8325-4}$ (x10$^7$) |
|---|---|---|---|---|---|
| $C_6H_5O$ | 26.9 | 4.4 | $C_3H_3$ | -2.5 | -0.8 |
| $C_3H_3O_2$ | 4.5 | 1.3 | $C_2H_3$ | -2.3 | -1.6 |
| $C_3H_3O$ | 2.7 | 0.6 | $C_8H_{15}$ | -2.2 | -1.1 |
| $C_2H_3O_2$ | 2.2 | 5.1 | $C_4H_7$ | -2.2 | -2.4 |
| $C_4H_5O_2$ | 2.0 | 8.4 | $C_3H_7$ | -2.1 | -2.0 |
| $C_6H_7O$ | 1.9 | 0.4 | $C_4H_5$ | -1.8 | -1.1 |
| $C_3H_7O$ | 1.4 | 7.4 | $CHO_2$ | -1.5 | -2.1 |
| $C_6H_{11}O_3$ | 1.3 | 4.4 | $C_2H_5$ | -1.4 | -1.0 |
| $C_5H_9$ | 1.0 | 3.6 | | | |
| $C_2H_3O$ | 0.8 | 3.8 | | | |

Fig. 3

| Composition:- monomers used and ratio | Bacterial performance:- ι % |
|---|---|
| 18' & 8' (2:1) | 2.65E-08 |
| 7' & 8' (2:1) | 1.08E-01 |
| 4' & 12' (2:1) | 1.11E-01 |
| 2' & 8' (2:1) | 1.14E-01 |
| 3' & 2' (2:1) | 1.18E-01 |
| 6' & 7' (2:1) | 1.28E-01 |
| 10' & 13' (2:1) | 1.34E-01 |
| 4' & 11' (2:1) | 1.37E-01 |
| 7' & 13' (2:1) | 1.38E-01 |
| 4' & 15' (2:1) | 1.41E-01 |
| 12' (homopolymer) | 1.53E-01 |
| 2' & 15' (2:1) | 1.59E-01 |
| 7' & 1' (2:1) | 1.62E-01 |
| 7' & 5' (2:1) | 1.63E-01 |
| 10' & 9' (2:1) | 1.65E-01 |
| 2' & 5' (2:1) | 1.65E-01 |
| 12' & 3' (2:1) | 1.65E-01 |
| 7' & 10' (2:1) | 1.67E-01 |
| 7' & 16' (2:1) | 1.70E-01 |
| 15' & 13' (2:1) | 1.72E-01 |

Fig. 9

Group (C)

Coated silicone catheters (■)
Uncoated silicone catheters (▨)

Poly(styrene) (■) (left hand bars)
Inventive compositions (■) (right hand bars)

POLYMERS WHICH RESIST BACTERIAL ATTACHMENT

CROSS-REFERENCE TO RELATED APPLICATIONS

This application is the U.S. National Stage of International Application PCT/GB2012/050987 filed May 4, 2012, which designates the U.S. and was published by the International Bureau in English on Nov. 8, 2012, and which claims the benefit of Great Britain Application No. 1107416.8, filed May 4, 2011, and Great Britain Application No. 1200832.2, filed Jan. 18, 2012, all of which are hereby incorporated by reference in their entirety.

The present invention relates to polymers and their use in inhibiting bacterial attachment, and in preventing or reducing biofilm formation.

BACKGROUND TO THE INVENTION

Biofilms are associations of microorganisms that develop on a surface. These represent a severe problem as they provide a microenvironment which contains excreted enzymes and other factors, allowing the bacteria to evade host immune responses, including antibodies and cellular immune responses. Further, biofilms can be extremely resistant to removal and disinfection and can act to exclude antibiotics.

Biofilms may involve an aggregation of a single bacterial species or may include more than one species of bacteria. Usually the bacteria are embedded in a layer of extracellular polymers in the form of a matrix.

Bacterial biofilm development on a surface is a process involving (i) exposure of the surface to planktonic bacterial cells; (ii) a two stage process of attachment of the bacteria to the surface; this involves a first stage of initial weak reversible attachment of the bacteria to the surface followed by a second stage of strong irreversible attachment to the surface; (iii) microcolony formation, which results from further growth and development of attached bacteria and includes bacterial translocation across the surface; (iv) macrocolony development, which involves the microcolony increasing in size to result in an organised structure with a distinct architecture; (v) dispersal of bacteria from the mature biofilm.

Hospital acquired infections are a major public health challenge throughout the world. It is estimated that 80% of the infections acquired in hospitals involve biofilms, within which bacteria show up to 1000 times higher resistance to antibiotic treatment and the host immune system when compared to their planktonic counterparts.

Advances in medical devices such as catheters, vascular access devices, peripheral lines, intravenous sites, drains, gastric feeding tubes, trachea tubes, stents, guidewires, pacemakers, and other implantable devices have enormously benefited the diagnostic and therapeutic practices in medical care. However, bacterial infections are becoming one of the most common and serious complications related to the use of implanted medical devices. For example, urinary-tract infection frequently occurs in patients with catheters in place for extended periods of time. Bacterial attachment can be mediated by the mineralisation of salt components within urine, as well as by the effects of non-mineral components, such as creatinine and urea, which can affect polymer surfaces and promote bacterial attachment.

Known strategies for reducing biofilm associated infections focus on the modification of existing materials used to manufacture indwelling medical devices by the introduction of antimicrobial compounds, such as antibiotics. These treatments will generally involve: 1) adsorption of an antimicrobial agent to the surface of the medical device; 2) incorporation of an antimicrobial agent into a polymer coating that is applied on the surface of the medical device; or 3) compounding an antimicrobial agent into the bulk material that is used to make the medical device.

These approaches are therefore based on the leaching of the active antimicrobial agent, which may be an antibiotic or a metal ion. The antimicrobial efficacy is therefore dependent on the loading of the active antimicrobial agent within the material and the rate of its release from the surface.

It is often very difficult to control the release rate and maintain a constant level of concentration at the surface, as the release rate depends on many factors, such as actual concentration, solubility, and ability to diffuse, and these may also change over the timescale during which the medical device is used.

Therefore, a simple and effective method to create a surface with intrinsic resistance against bacterial attachment and biofilm formation is needed.

SUMMARY OF THE INVENTION

The present invention has identified that greater efficacy in preventing biofilm formation could be realised by the design of new materials with inherent resistance to bacterial attachment. These would then be able to prevent biofilm formation at an earlier stage of development.

Therefore materials have been developed which inhibit bacterial attachment, and therefore can be used to prevent or reduce biofilm formation.

The invention provides a method for inhibiting bacterial attachment to a surface, the method comprising forming the surface from a polymer, or applying a polymer to the surface, wherein the polymer is a homopolymer formed from a (meth) acrylate or (meth) acrylamide monomer or a copolymer formed from one or more (meth) acrylate or (meth) acrylamide monomers, wherein the (meth) acrylate or (meth) acrylamide monomers are of formula (I) or (II):

wherein
n is 1, 2 or 3,
R' is independently H or $CH_3$,
R is an organic group having a total of from 2 to 24 carbon atoms, wherein the organic group includes an aliphatic or aromatic hydrocarbon moiety and wherein the organic group does not include any hydroxyl groups.

The invention also provides the use of a polymer to inhibit bacterial attachment to a surface, wherein the polymer is a homopolymer formed from a (meth) acrylate or (meth) acrylamide monomer or a copolymer formed from one or more (meth) acrylate or (meth) acrylamide monomers, wherein the (meth) acrylate or (meth) acrylamide monomers are of formula (I) or (II).

The invention also provides a method for preventing or reducing biofilm formation on a surface, the method comprising forming the surface from a polymer, or applying a polymer to the surface, wherein the polymer is a homopolymer formed from a (meth) acrylate or (meth) acrylamide monomer or a copolymer formed from one or more (meth) acrylate or (meth) acrylamide monomers, wherein the (meth) acrylate or (meth) acrylamide monomers are of formula (I) or (II).

The invention also provides the use of a polymer to prevent or reduce biofilm formation on a surface, wherein the polymer is a homopolymer formed from a (meth) acrylate or (meth) acrylamide monomer or a copolymer formed from one or more (meth) acrylate or (meth) acrylamide monomers, wherein the (meth) acrylate or (meth) acrylamide monomers are of formula (I) or (II).

The invention also provides an article having a surface that is made of a polymer or that has a polymer coating, wherein the polymer is a homopolymer formed from a (meth) acrylate or (meth) acrylamide monomer or a copolymer formed from one or more (meth) acrylate or (meth) acrylamide monomers, wherein the (meth) acrylate or (meth) acrylamide monomers are of formula (I) or (II).

The article may in one embodiment be a medical device. This may be a device that will come into direct contact with the human or animal body, such as a surgical instrument or an implant or prosthesis. This may alternatively be a medical device that will not directly come into contact with the inside of the human or animal body.

The polymers of the type used in the present invention are based on (meth)acrylate or (meth) acrylamide monomers containing aliphatic or aromatic carbon fragments. These have been shown to successfully inhibit bacterial attachment for pathogens that cause urinary tract infections and other infections. In particular, these have been shown to successfully inhibit bacterial attachment for the pathogens *Pseudomonas aeruginosa*, *Staphylococcus aureus* and *Escherichia coli* (including uropathogenic *Escherichia coli*). The effects of the polymers include resistance to bacterial attachment that is mediated by the mineralisation of salt components within urine. The effects of the polymers also include resistance to bacterial attachment that is mediated by non-mineral components within urine, such as creatinine and urea, which can affect polymer surface and promote attachment.

DETAILED DESCRIPTION OF THE INVENTION

The polymers used in the present invention are homopolymers formed from a (meth) acrylate or (meth) acrylamide monomer or copolymers formed from one or more (meth) acrylate or (meth) acrylamide monomers, wherein the (meth) acrylate or (meth) acrylamide monomers are of formula (I) or (II):

$$[H_2C=CR'—C(=O)—O—]_nR \quad (I)$$

$$[H_2C=CR'—C(=O)—NH—]_nR \quad (II)$$

wherein
n is 1, 2 or 3,
R' is independently H or $CH_3$,
R is an organic group having a total of from 2 to 24 carbon atoms, wherein the organic group includes an aliphatic or aromatic hydrocarbon moiety and wherein the organic group does not include any hydroxyl groups.

BRIEF DESCRIPTION OF THE DRAWINGS

FIG. 2(A) is for PA01 ($R^2$=0.71), FIG. 2(B) is for *S. aureus* 8325-4 ($R^2$=0.74), FIG. 2(C) is for UPEC($R^2$=0.6) and FIG. 2(D) is for τ ($R^2$=0.87) in RPMI. The y=x line is drawn as a guide.

FIG. 3 shows the key ions identified in Example 1, by ToF-SIMS analysis combined with PLS analysis, as being important for bacterial attachment to surfaces, for both PAO1 and *S. aureus*.

FIG. 9 shows the bacterial performance (τ) values for the top 20 compositions from the second generation array in Example 2.

Figure 1:
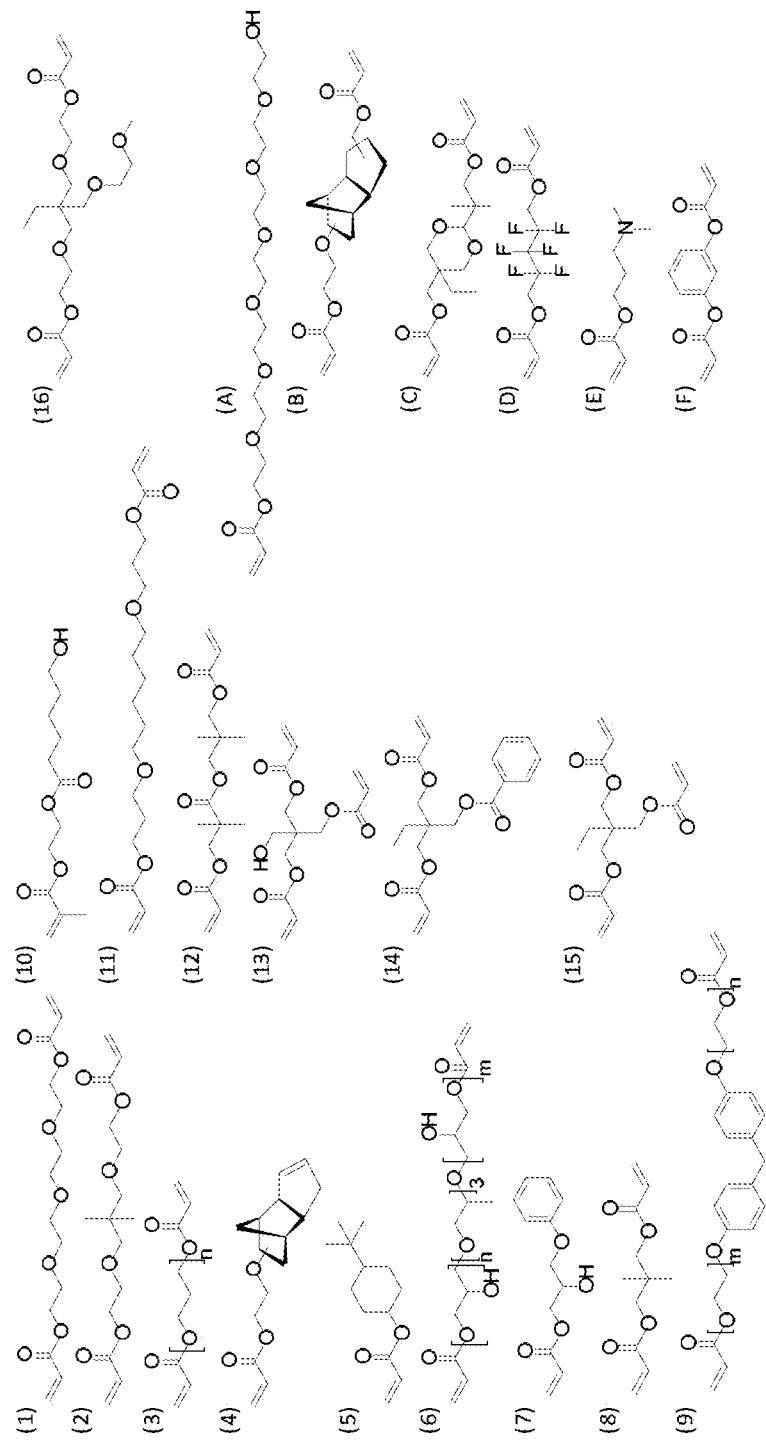
FIG. 1 shows the monomers 1-16 and the monomers A-F that were used in the first generation assay of Example 1.

When the polymer is a homopolymer, it is of course formed from 100 wt % of the same monomer, which is a monomer of formula (I) or (II). When the polymer is a copolymer, it is formed from two or more different monomers. Preferably 50 wt % or more of the monomers used to form the copolymer are monomers of formula (I) or (II), such as 55 wt % or more, 60 wt % or more, or 65 wt % or more. In one preferred embodiment, 70 wt % or more, such as 75 wt % or more, 80 wt % or more, 85 wt % or more, or 90 wt % or more, or 95 wt % or more, or 99 wt % or more, of the monomers used to form the copolymer are monomers of formula (I) or (II). Most preferably, 100 wt % of the monomers used to form the copolymer are monomers of formula (I) or (II).

In one embodiment, some or all of the monomers used to form the polymer are monomers of formula (I) or (II) where n is 1 or 2. It may be that 100% of the monomers used to form the polymer are monomers of formula (I) or (II) where n is 1 or 2.

In one preferred embodiment, some or all of the monomers used to form the polymer are monomers of formula (I) or (II) where R is an organic group that includes an aliphatic hydrocarbon moiety and optionally further includes an aromatic hydrocarbon moiety. Particularly beneficial results have been obtained when there is an aliphatic moiety present.

In particular, superior efficacy to prevent bacterial attachment has been demonstrated for polymers where the R group includes one or more hydrophobic moiety. The use of polymers that include hydrophobic moieties on a polyacrylate/polyacrylamide backbone that contains weakly polar ester or amide groups, which exhibit an amphiphilic chemical nature, is particularly beneficial.

In one embodiment, some or all of the monomers used to form the polymer are monomers of formula (I) or (II) where R is an organic group that only includes moieties selected from: alkyl, alkenyl, carbonyl, ether, ester, phenyl, cycloalkyl, cycloalkenyl and heterocycloalkyl moieties, each of which may optionally be halogenated.

The skilled reader will appreciate that one such moiety may by itself form the organic group R, (for example, the organic group R may be solely made up of an alkyl or cycloalkyl moiety), or that two or more such moieties may be combined to form the organic group R (for example, the organic group R may be made up of an alkyl moiety and a phenyl moiety, or a cycloalkyl moiety and an alkyl moiety). There may be two or more of the same type of moiety present within the organic group (for example there may be an alkyl moiety and two phenyl moieties, forming a bisphenol unit).

The alkyl moieties are preferably C1-C12 moieties. The alkenyl moieties are preferably C2-C12 moieties. The cycloalkyl moieties are preferably C5-C12 moieties. The cycloalkenyl moieties are preferably C5-C12 moieties. The heterocycloalkyl moieties are preferably C5-C12 moieties. When there is halo substitution of a moiety, the halo groups may suitably be selected from fluoro, chloro and bromo, for example they may be fluoro.

It may be that 20 wt % or more (such as 25 wt % or more, 30 wt % or more, 33 wt % or more, or 40 wt % or more) of the monomers used to form the polymer are monomers of formula (I) or (II) where R is an organic group that only includes moieties selected from: alkyl, alkenyl, carbonyl, ether, ester, phenyl, cycloalkyl, cycloalkenyl and heterocycloalkyl moieties, each of which may optionally be halogenated. Preferably, 50 wt % or more (such as 55 wt % or more, 60 wt % or more, or 65 wt % or more) of the monomers used to form the polymer are monomers of formula (I) or (II) where R is an organic group that only includes moieties selected from: alkyl, alkenyl, carbonyl, ether, ester, phenyl, cycloalkyl, cycloalkenyl and heterocycloalkyl moieties, each of which may optionally be halogenated.

In one preferred embodiment, 70 wt % or more, such as 75 wt % or more, 80 wt % or more, 85 wt % or more, or 90 wt % or more, or 95 wt % or more, or 99 wt % or more, of the monomers used to form the polymer are monomers of formula (I) or (II) where R is an organic group that only includes moieties selected from: alkyl, alkenyl, carbonyl, ether, ester, phenyl, cycloalkyl, cycloalkenyl and heterocycloalkyl moieties, each of which may optionally be halogenated.

Most preferably, 100 wt % of the monomers used to form the polymer are monomers of formula (I) or (II) where R is an organic group that only includes moieties selected from: alkyl, alkenyl, carbonyl, ether, ester, phenyl, cycloalkyl, cycloalkenyl and heterocycloalkyl moieties, each of which may optionally be halogenated.

In one embodiment some or all of the monomers used to form the polymer are monomers of formula (I) or (II) where R is an organic group having a total of from 2 to 20 carbon atoms, such as from 2 to 18 or from 2 to 16, e.g. from 2 to 12 carbon atoms.

It may, for example, be that the polymer is formed from one monomer of formula (I) or (II) where R is an organic group having a total of from 2 to 16 (e.g. from 2 to 12) carbon atoms and from one monomer of formula (I) or (II) where R is an organic group having a total of from 2 to 24 carbon atoms.

Preferably 20 wt % or more (such as 25 wt % or more, 30 wt % or more, 33 wt % or more, or 40 wt % or more) of the monomers used to form the polymer are monomers of formula (I) where R is an organic group having a total of from 2 to 20 carbon atoms, such as from 2 to 18 or from 2 to 16, e.g. from 2 to 12 carbon atoms. In one embodiment, 50 wt % or more (such as 55 wt % or more, 60 wt % or more, or 65 wt % or more) of the monomers used to form the polymer are monomers of formula (I) or (II) where R is an organic group having a total of from 2 to 20 carbon atoms, such as from 2 to 18 or from 2 to 16, e.g. from 2 to 12 carbon atoms.

In one preferred embodiment, 70 wt % or more, such as 75 wt % or more, 80 wt % or more, 85 wt % or more, or 90 wt % or more, or 95 wt % or more, or 99 wt % or more, of the monomers used to form the copolymer are monomers of formula (I) or (II) where R is an organic group having a total of from 2 to 20 carbon atoms, such as from 2 to 18 or from 2 to 16, e.g. from 2 to 12 carbon atoms. Most preferably, 100 wt % of the monomers used to form the copolymer are monomers of formula (I) or (II) where R is an organic group having a total of from 2 to 20 carbon atoms, such as from 2 to 18 or from 2 to 16, e.g. from 2 to 12 carbon atoms.

In one embodiment some or all of the monomers used to form the polymer are monomers of formula (I) or (II) where R is an organic group that includes an aliphatic hydrocarbon moiety which is a C1-C16 straight or branched chain alkyl moiety, or a C5-C16 cycloalkyl moiety, or a C5-C16 cycloalkenyl moiety, such as a C1-C12 straight or branched chain alkyl moiety, or a C5-C12 cycloalkyl moiety or a C5-C12 cycloalkenyl moiety.

Preferably 20 wt % or more (such as 25 wt % or more, 30 wt % or more, 33 wt % or more, or 40 wt % or more) of the monomers used to form the polymer are monomers of formula (I) or (II) where R is an organic group that includes an aliphatic hydrocarbon moiety which is a C1-C16 straight or branched chain alkyl moiety, or a C5-C16 cycloalkyl moiety or a C5-C16 cycloalkenyl moiety, such as a C1-C12 straight or branched chain alkyl moiety, or a C5-C12 cycloalkyl moiety or a C5-C12 cycloalkenyl moiety. In one embodiment, 50 wt % or more (such as 55 wt % or more, 60 wt % or more, or 65 wt % or more) of the monomers used to form the polymer are monomers of formula (I) or (II) where R is an organic group that includes an aliphatic hydrocarbon moiety which is a C1-C16 straight or branched chain alkyl moiety, or a C5-C16 cycloalkyl moiety or a C5-C16 cycloalkenyl moiety, such as a C1-C12 straight or branched chain alkyl moiety, or a C5-C12 cycloalkyl moiety or a C5-C12 cycloalkenyl moiety.

In one preferred embodiment, 70 wt % or more, such as 75 wt % or more, 80 wt % or more, 85 wt % or more, or 90 wt % or more, or 95 wt % or more, or 99 wt % or more, of the monomers used to form the copolymer are monomers of formula (I) or (II) where R is an organic group that includes an aliphatic hydrocarbon moiety which is a C1-C16 straight or branched chain alkyl moiety, or a C5-C16 cycloalkyl moiety or a C5-C16 cycloalkenyl moiety, such as a C1-C12 straight or branched chain alkyl moiety, or a C5-C12 cycloalkyl moiety or a C5-C12 cycloalkenyl moiety. Most preferably, 100 wt % of the monomers used to form the copolymer are monomers of formula (I) or (II) where R is an organic group that includes an aliphatic hydrocarbon moiety which is a C1-C16 straight or branched chain alkyl moiety, or a C5-C16 cycloalkyl moiety or a C5-C16 cycloalkenyl moiety, such as a C1-C12 straight or branched chain alkyl moiety, or a C5-C12 cycloalkyl moiety or a C5-C12 cycloalkenyl moiety.

In one embodiment some or all of the monomers used to form the polymer are monomers of formula (I) or (II) where R is an organic group that includes an aliphatic hydrocarbon moiety which is a C1-C16 straight or branched chain alkyl moiety, or a C5-C16 cycloalkyl moiety, such as a C1-C12 straight or branched chain alkyl moiety, or a C5-C12 cycloalkyl moiety.

Preferably 20 wt % or more (such as 25 wt % or more, 30 wt % or more, 33 wt % or more, or 40 wt % or more) of the monomers used to form the polymer are monomers of formula (I) or (II) where R is an organic group that includes an aliphatic hydrocarbon moiety which is a C1-C16 straight or branched chain alkyl moiety, or a C5-C16 cycloalkyl moiety, such as a C1-C12 straight or branched chain alkyl moiety, or a C5-C12 cycloalkyl moiety. In one embodiment, 50 wt % or more (such as 55 wt % or more, 60 wt % or more, or 65 wt % or more) of the monomers used to form the polymer are monomers of formula (I) or (II) where R is an organic group that includes an aliphatic hydrocarbon moiety which is a C1-C16 straight or branched chain alkyl moiety, or a C5-C16 cycloalkyl moiety, such as a C1-C12 straight or branched chain alkyl moiety, or a C5-C12 cycloalkyl moiety.

In one preferred embodiment, 70 wt % or more, such as 75 wt % or more, 80 wt % or more, 85 wt % or more, or 90 wt % or more, or 95 wt % or more, or 99 wt % or more, of the monomers used to form the copolymer are monomers of formula (I) or (II) where R is an organic group that includes an aliphatic hydrocarbon moiety which is a C1-C16 straight or branched chain alkyl moiety, or a C5-C16 cycloalkyl moiety, such as a C1-C12 straight or branched chain alkyl moiety, or a C5-C12 cycloalkyl moiety. Most preferably, 100 wt % of the monomers used to form the copolymer are monomers of formula (I) or (II) where R is an organic group that includes an aliphatic hydrocarbon moiety which is a C1-C16 straight or branched chain alkyl moiety, or a C5-C16 cycloalkyl moiety, such as a C1-C12 straight or branched chain alkyl moiety, or a C5-C12 cycloalkyl moiety.

In one embodiment, the monomers used are (meth) acrylate monomers. In another embodiment, the monomers used are (meth) acrylamide monomers. In another embodiment, a copolymer formed from one or more (meth) acrylate monomers and one or more (meth) acrylamide monomers is used.

In one embodiment, some or all of the monomers used to form the polymer are monomers of formula (I).

Preferably 20 wt % or more (such as 25 wt % or more, 30 wt % or more, 33 wt % or more, or 40 wt % or more) of the monomers used to form the polymer are monomers of formula (I). In one embodiment, 50 wt % or more (such as 55 wt % or more, 60 wt % or more, or 65 wt % or more) of the monomers used to form the polymer are monomers of formula (I).

In one preferred embodiment, 70 wt % or more, such as 75 wt % or more, 80 wt % or more, 85 wt % or more, or 90 wt % or more, or 95 wt % or more, or 99 wt % or more, of the monomers used to form the copolymer are monomers of formula (I). Most preferably, 100 wt % of the monomers used to form the copolymer are monomers of formula (I).

In one embodiment, some or all of the monomers used to form the polymer are monomers of formula (I) selected from the following groups (A) and (B):

Group (A)

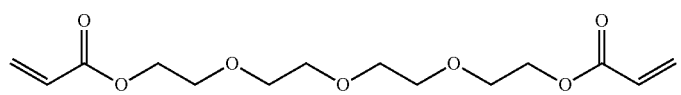

(1)

-continued
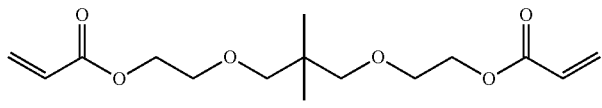
(2)
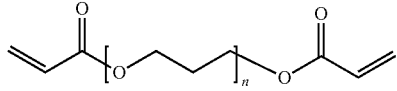
(3)
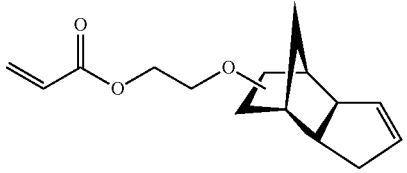
(4)
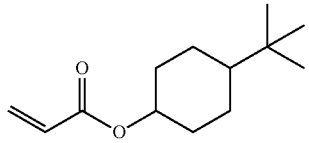
(5)
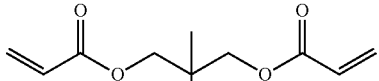
(8)
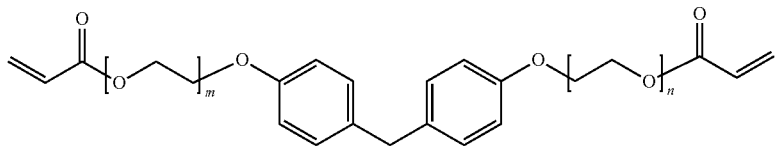
(9)
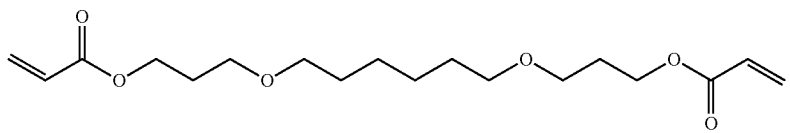
(11)
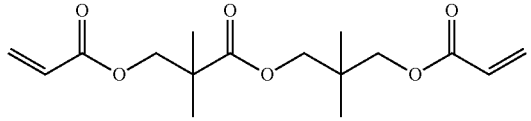
(12)
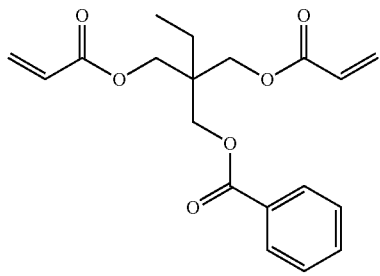
(14)
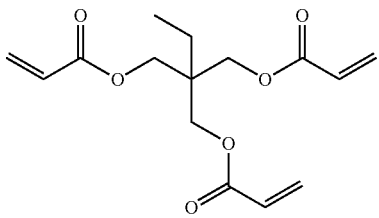
(15)
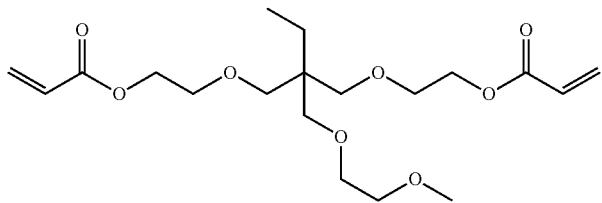
(16)
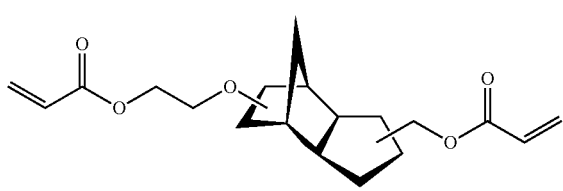
(B)

-continued
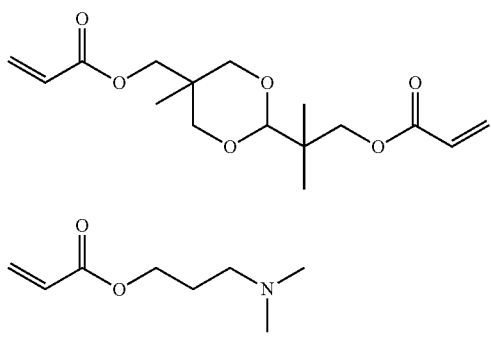
(C)
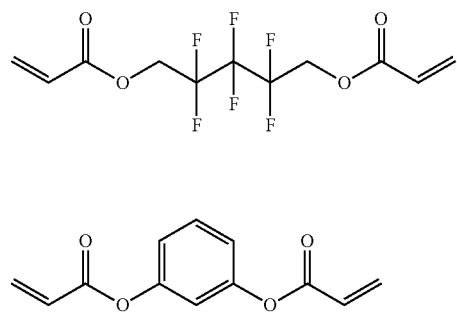
(D)
(E)
(F)
Group (B)
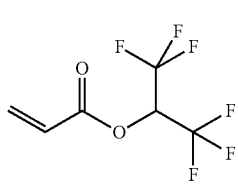
(1')
(2')
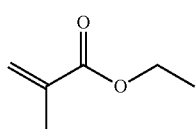
(3')
(4')
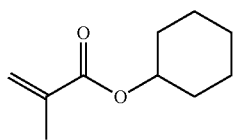
(5')
(6')
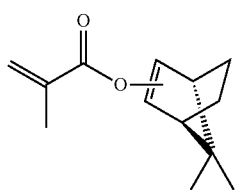
(7')
(8')
(9')
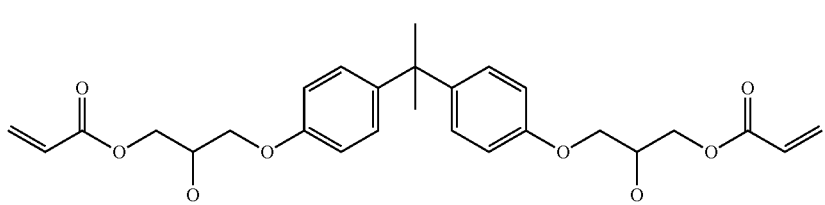
(10')
(11')
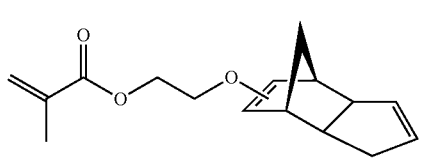
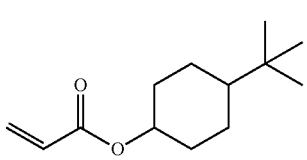

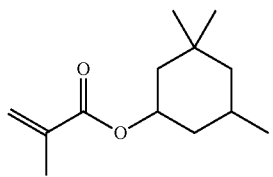
(12')

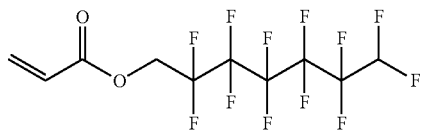
(13')

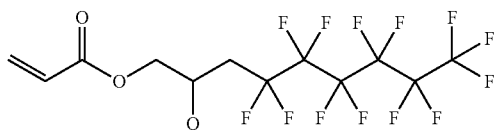
(14')

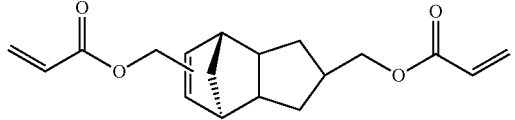
(15')

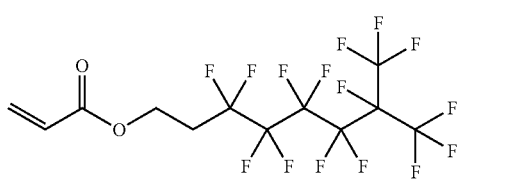
(16')

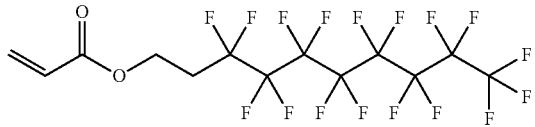
(17')

(18')

Preferably 20 wt % or more (such as 25 wt % or more, 30 wt % or more, 33 wt % or more, or 40 wt % or more) of the monomers used to form the polymer are monomers of formula (I) selected from Groups A and B. In one embodiment, 50 wt % or more (such as 55 wt % or more, 60 wt % or more, or 65 wt % or more) of the monomers used to form the polymer are monomers of formula (I) selected from Groups A and B. In one preferred embodiment, 70 wt % or more, such as 75 wt % or more, 80 wt % or more, 85 wt % or more, or 90 wt % or more, or 95 wt % or more, or 99 wt % or more, of the monomers used to form the polymer are monomers of formula (I) selected from Groups A and B. Most preferably, 100 wt % of the monomers used to form the copolymer are monomers of formula (I) selected from Groups A and B.

In one embodiment, some or all of the monomers used to form the polymer are monomers of formula (I) selected from monomers 4, 5, 8, 15 and B of group (A) and monomers 1', 2', 3', 4', 5', 6', 7', 8', 9', 10', 11', 12', 13', 15', 16' and 18' of group (B).

Preferably 20 wt % or more (such as 25 wt % or more, 30 wt % or more, 33 wt % or more, or 40 wt % or more) of the monomers used to form the polymer are monomers of formula (I) selected from monomers 4, 5, 8, 15 and B of group (A) and monomers 1, 2, 3, 4, 5, 6, 7, 8, 9, 10, 11, 12, 13, 15, 16 and 18 of group (B). In one embodiment, 50 wt % or more (such as 55 wt % or more, 60 wt % or more, or 65 wt % or more) of the monomers used to form the polymer are monomers of formula (I) selected from selected from monomers 4, 5, 8, 15 and B of group (A) and monomers 1', 2', 3', 4', 5', 6', 7', 8', 9', 10', 11', 12', 13', 15', 16' and 18' of group (B).

In one preferred embodiment, 70 wt % or more, such as 75 wt % or more, 80 wt % or more, 85 wt % or more, or 90 wt % or more, or 95 wt % or more, or 99 wt % or more, of the monomers used to form the polymer are monomers of formula (I) selected from selected from monomers 4, 5, 8, 15 and B of group (A) and monomers 1', 2', 3', 4', 5', 6', 7', 8', 9', 10', 11', 12', 13', 15', 16' and 18' of group (B). Most preferably, 100 wt % of the monomers used to form the polymer are monomers of formula (I) selected from selected from monomers 4, 5, 8, 15 and B of group (A) and monomers 1', 2', 3', 4', 5', 6', 7', 8', 9', 10', 11', 12', 13', 15', 16' and 18' of group (B).

In one preferred embodiment, 50 wt % or more, such as 55 wt % or more, 60 wt % or more, 65 wt % or more, or 70 wt % or more, or 75 wt % or more, or 80 wt % or more, of the monomers used to form the polymer are monomers of formula (I) selected from selected from monomers 6', 7', and 15' of group (B), and especially monomers 7' and 15' of group (B). In one embodiment the polymer is a homopolymer of monomer 7' of group (B), or a copolymer including at least 70% wt of monomer 7' of group (B) (wherein preferably the second monomer is selected from monomers 4, 5, 8, 15 and B of group (A) and monomers 1', 2', 3', 4', 5', 6', 8', 9', 10', 11', 12', 13', 15', 16' and 18' of group (B)), or a homopolymer of monomer 15' of group (B), or a copolymer including at least 70% wt of monomer 15' of group (B) (wherein preferably the second monomer is selected from monomers 4, 5, 8, 15 and B of group (A) and monomers 1', 2', 3', 4', 5', 6', 7', 8', 9', 10', 11', 12', 13', 16' and 18' of group (B)). It may be that the polymer is a homopolymer of monomer 7' of group (B), or a copolymer including at least 75% wt of monomer 7' of group (B) (wherein preferably the second monomer is selected from monomers 4, 5, 8, 15 and B of group (A) and monomers 1', 2', 3', 4', 5', 6', 7', 8', 9', 10', 11', 12', 13', 15', 16' and 18' of group (B)), or a homopolymer of monomer 15' of group (B).

In one preferred embodiment the polymer is (a) a homopolymer of a monomer of formula (I) selected from monomers 4, 5, 8, 15 and B of group (A) and monomers 1', 2', 3', 4', 5', 6', 7', 8', 9', 10', 11', 12', 13', 15', 16' and 18' of group (B); or (b) a copolymer wherein 70 wt % or more (e.g. 75 wt % or more) of the monomers used to form the polymer are selected from monomers 4, 5, 8, 15 and B of group (A) and monomers 1', 2', 3', 4', 5', 6', 7', 8', 9', 10', 11', 12', 13', 15', 16' and 18' of group (B).

In one such embodiment the polymer is (a) a homopolymer of a monomer of formula (I) selected from monomers 4, 5, 8, and B of group (A) and monomers 7', 12' and 15' of group (B); or (b) a copolymer wherein 70 wt % or more (e.g. 75 wt % or more) of the monomers used to form the polymer are selected from monomers 4, 5, 8, 15 and B of group (A) and monomers 1', 2', 3', 4', 5', 6', 7', 8', 9', 10', 11', 12', 13', 15', 16' and 18' of group (B).

It may be that the polymer is (a) a homopolymer of a monomer of formula (I) selected from monomers 4, 5, 8, 15 and B of group (A) and monomers 1', 2', 3', 4', 5', 6', 7', 8', 9', 10', 11', 12', 13', 15', 16' and 18' of group (B); or (b) a copolymer wherein 70 wt % or more (e.g. 75 wt % or more) of the monomers used to form the polymer are selected from monomers 4, 5, 8, 15 and B of group (A) and monomers 1', 2', 3', 4', 5', 6', 7', 8', 9', 10', 11', 12', 13', 15', 16' and 18' of group (B) and all of the monomers used to form the polymer are monomers of formula (I).

In one such embodiment the polymer is (a) a homopolymer of a monomer of formula (I) selected from monomers 4, 5, 8, and B of group (A) and monomers 7', 12' and 15' of group (B); or (b) a copolymer wherein 70 wt % or more (e.g. 75 wt % or more) of the monomers used to form the polymer are selected from monomers 4, 5, 8, 15 and B of group (A) and monomers 1', 2', 3', 4', 5', 6', 7', 8', 9', 10', 11', 12', 13', 15', 16' and 18' of group (B) and all of the monomers used to form the polymer are monomers of formula (I).

Co-monomers that are of formula (I) but that are not in group (A) or (B) include, but are not limited to, di(ethylene glycol) methyl ether methacrylate, ethylene glycol methyl ether methacrylate, ethylene glycol methyl ether acrylate and di(ethylene glycol) ethyl ether acrylate. Such co-monomers may, for example, be selected to achieve desired properties such as improved flexibility. For example, such co-monomers may be used to lower the polymer's glass transition temperature ($T_g$) to below room temperature.

Preferably co-monomers that are of formula (I) but that are not in group (A) or (B) are used in amounts of 30 wt % or less, e.g. from 0 to 28 wt % or from 1 to 25 wt %.

In one embodiment some or all of the monomers used to form the polymer are monomers of formula (I) selected from monomers 6', 7' and 15' of Group (B). It may be that 70 wt % or more (e.g. 75 wt % or more) of the monomers used to form the polymer are monomers of formula (I) selected from monomers 7' and 15' of Group (B). It may be that the polymer is a homopolymer formed from monomer 7' of group B, or a homopolymer formed from monomer 15' of Group (B), or a copolymer formed from monomer 7' and a further monomer of formula (I), e.g. a further monomer from Group (B). In this copolymer preferably 70 wt % or more (e.g. 75 wt % or more) of the monomers used to form the polymer are monomer 7'.

It may be that the polymer is a homopolymer formed from monomer 7' of group (B), or a homopolymer formed from monomer 15' of Group B, or a copolymer formed from monomer 7' and monomer 6' of Group (B). In this copolymer preferably 70 wt % or more (e.g. 75 wt % or more) of the monomers used to form the polymer are monomer 7'.

In one embodiment, the polymer is selected from the group consisting of:
1. the homopolymer of monomer 4 of group (A).
2. the homopolymer of monomer 5 of group (A).
3. the homopolymer of monomer 8 of group (A).
4. the homopolymer of monomer B of group (A).
5. copolymers of monomer B of group (A) with monomer 4 of group (A); preferably with from 5:95 to 95:5 (wt/wt) monomer B:monomer 4, e.g. from 20:80 to 95:5 or from 40:60 to 90:10 or from 50:50 to 70:30 (wt/wt) monomer B:monomer 4, such as 60:40 (wt/wt) monomer B:monomer 4.
6. copolymers of monomer B of group (A) with monomer 5 of group (A) preferably with from 5:95 to 95:5 (wt/wt) monomer B:monomer 5, e.g. from 20:80 to 95:5 or from 40:60 to 90:10 or from 50:50 to 75:25 (wt/wt) monomer B:monomer 5, such as 70:30 (wt/wt) monomer B:monomer 5.
7. copolymers of monomer B of group (A) with monomer 8 of group (A) preferably with from 5:95 to 95:5 (wt/wt) monomer B:monomer 8, e.g. from 20:80 to 95:5 or from 40:60 to 90:10 or from 50:50 to 70:30 (wt/wt) monomer B:monomer 8, such as 60:40 (wt/wt) monomer B:monomer 8.
8. copolymers of monomer 18' of group (B) with monomer 8' of group (B) preferably with from 5:95 to 95:5 (wt/wt) monomer 18':monomer 8', e.g. from 20:80 to 95:5 or from 40:60 to 90:10 or from 50:50 to 70:30 (wt/wt) monomer 18':monomer 8', such as a 2:1 (wt/wt) ratio monomer 18':monomer 8'.
9. copolymers of monomer 7' of group (B) with monomer 8' of group (B) preferably with from 5:95 to 95:5 (wt/wt) monomer 7':monomer 8', e.g. from 20:80 to 95:5 or from 40:60 to 90:10 or from 50:50 to 70:30 (wt/wt) monomer 7':monomer 8', such as a 2:1 (wt/wt) ratio monomer 7':monomer 8'.
10. copolymers of monomer 4' of group (B) with monomer 12' of group (B) preferably with from 5:95 to 95:5 (wt/wt) monomer 4':monomer 12', e.g. from 20:80 to 95:5 or from 40:60 to 90:10 or from 50:50 to 70:30 (wt/wt) monomer 4':monomer 12', such as a 2:1 (wt/wt) ratio monomer 4':monomer 12'.
11. copolymers of monomer 2' of group (B) with monomer 8' of group (B) preferably with from 5:95 to 95:5 (wt/wt) monomer 2':monomer 8', e.g. from 20:80 to 95:5 or from 40:60 to 90:10 or from 50:50 to 70:30 (wt/wt) monomer 2':monomer 8', such as a 2:1 (wt/wt) ratio monomer 2':monomer 8'.
12. copolymers of monomer 3' of group (B) with monomer 2' of group (B) preferably with from 5:95 to 95:5 wt/wt) monomer 3':monomer 2', e.g. from 20:80 to 95:5 or from 40:60 to 90:10 or from 50:50 to 70:30 (wt/wt) monomer 3':monomer 2', such as a 2:1 (wt/wt) ratio monomer 3':monomer 2'.
13. copolymers of monomer 6' of group (B) with monomer 7' of group (B) preferably with from 5:95 to 95:5 (wt/wt) monomer 6':monomer 7', e.g. from 20:80 to 95:5 or from 40:60 to 90:10 or from 50:50 to 70:30 (wt/wt) monomer 6':monomer 7', such as a 2:1 (wt/wt) ratio monomer 6':monomer 7'.
14. copolymers of monomer 10' of group (B) with monomer 13' of group (B) preferably with from 5:95 to 95:5 (wt/wt) monomer 10':monomer 13', e.g. from 20:80 to 95:5 or from 40:60 to 90:10 or from 50:50 to 70:30 (wt/wt) monomer 10':monomer 13', such as a 2:1 (wt/wt) ratio monomer 10':monomer 13'.
15. copolymers of monomer 4' of group (B) with monomer 11' of group (B) preferably with from 5:95 to 95:5 (wt/wt) monomer 4':monomer 11', e.g. from 20:80 to 95:5 or from 40:60 to 90:10 or from 50:50 to 70:30 (wt/wt) monomer 4':monomer 11', such as a 2:1 (wt/wt) ratio monomer 4':monomer 11'.
16. copolymers of monomer 7' of group (B) with monomer 13' of group (B) preferably with from 5:95 to 95:5 (wt/wt) monomer 7':monomer 13', e.g. from 20:80 to 95:5 or from 40:60 to 90:10 or from 50:50 to 70:30 (wt/wt) monomer 7':monomer 13', such as a 2:1 (wt/wt) ratio monomer 7':monomer 13'.
17. copolymers of monomer 4' of group (B) with monomer 15' of group (B) preferably with from 5:95 to 95:5 (wt/wt) monomer 4':monomer 15', e.g. from 20:80 to 95:5 or from 40:60 to 90:10 or from 50:50 to 70:30 (wt/wt) monomer 4':monomer 15', such as a 2:1 (wt/wt) ratio monomer 4':monomer 15'.
18. copolymers of monomer 2' of group (B) with monomer 15' of group (B) preferably with from 5:95 to 95:5 (wt/wt) monomer 2':monomer 15', e.g. from 20:80 to 95:5 or from 40:60 to 90:10 or from 50:50 to 70:30 (wt/wt) monomer 2':monomer 15', such as a 2:1 (wt/wt) ratio monomer 2':monomer 15'.
19. copolymers of monomer 7' of group (B) with monomer 1' of group (B) preferably with from 5:95 to 95:5 (wt/wt) monomer 7':monomer 1', e.g. from 20:80 to 95:5 or from 40:60 to 90:10 or from 50:50 to 70:30 (wt/wt) monomer 7':monomer 1', such as a 2:1 (wt/wt) ratio monomer 7':monomer 1'.
20. copolymers of monomer 7' of group (B) with monomer 5' of group (B) preferably with from 5:95 to 95:5 (wt/wt) monomer 7':monomer 5', e.g. from 20:80 to 95:5 or from 40:60 to 90:10 or from 50:50 to 70:30 (wt/wt) monomer 7':monomer 5', such as a 2:1 (wt/wt) ratio monomer 7':monomer 5'.
21. copolymers of monomer 10' of group (B) with monomer 9' of group (B) preferably with from 5:95 to 95:5 (wt/wt) monomer 10':monomer 9', e.g. from 20:80 to 95:5 or from 40:60 to 90:10 or from 50:50 to 70:30 (wt/wt) monomer 10':monomer 9', such as a 2:1 (wt/wt) ratio monomer 10':monomer 9'.
22. copolymers of monomer 2' of group (B) with monomer 5' of group (B) preferably with from 5:95 to 95:5 (wt/wt) monomer 2':monomer 5', e.g. from 20:80 to 95:5 or from 40:60 to 90:10 or from 50:50 to 70:30 (wt/wt) monomer 2':monomer 5', such as a 2:1 (wt/wt) ratio monomer 2':monomer 5'.
23. copolymers of monomer 12' of group (B) with monomer 3' of group (B) preferably with from 5:95 to 95:5 (wt/wt) monomer 12':monomer 3', e.g. from 20:80 to 95:5 or from 40:60 to 90:10 or from 50:50 to 70:30 (wt/wt) monomer 12':monomer 3', such as a 2:1 (wt/wt) ratio monomer 12':monomer 3'.
24. copolymers of monomer 7' of group (B) with monomer 10' of group (B) preferably with from 5:95 to 95:5 (wt/wt) monomer 7':monomer 10', e.g. from 20:80 to 95:5 or from 40:60 to 90:10 or from 50:50 to 70:30 (wt/wt) monomer 7':monomer 10', such as a 2:1 (wt/wt) ratio monomer 7':monomer 10'.
25. copolymers of monomer 7' of group (B) with monomer 16' of group (B) preferably with from 5:95 to 95:5 (wt/wt) monomer 7':monomer 16', e.g. from 20:80 to 95:5 or from 40:60 to 90:10 or from 50:50 to 70:30 (wt/wt) monomer 7':monomer 16', such as a 2:1 (wt/wt) ratio monomer 7':monomer 16'.
26. copolymers of monomer 15' of group (B) with monomer 13' of group (B) preferably with from 5:95 to 95:5 (wt/wt) monomer 15':monomer 13', e.g. from 20:80 to 95:5 or from 40:60 to 90:10 or from 50:50 to 70:30 (wt/wt) monomer 15':monomer 13', such as a 2:1 (wt/wt) ratio monomer 15':monomer 13'.
27. the homopolymer of monomer 12' of group (B).

The polymer may also selected from the group consisting of:
28. the homopolymer of monomer 7' of group (B).
29. the homopolymer of monomer 15' of group (B).
30. copolymers of monomer 7' of group (B) with monomer 6' of group (B); preferably with from 5:95 to 95:5 (wt/wt) monomer 7':monomer 6', e.g. from 20:80 to 95:5 or from 40:60 to 90:10 or from 50:50 to 80:20 (wt/wt) monomer 7':monomer 6', such as from 70:30 to 80:20 (wt/wt) monomer 7':monomer 6'.

Therefore in one embodiment the polymer is one of the polymers 1 to 30 in the lists above.

In one embodiment some or all of the monomers used to form the polymer are monomers of formula (I) or (II) where R is an organic group that includes moieties selected from: cyclic and aromatic moieties, each of which may optionally be halogenated. Preferably 20 wt % or more (such as 25 wt % or more, 30 wt % or more, 33 wt % or more, or 40 wt % or more); more preferably 50 wt % or more (such as 55 wt % or more, 60 wt % or more, or 65 wt % or more); and most preferably 70 wt % or more (such as 75 wt % or more, 80 wt % or more, 85 wt % or more, or 90 wt % or more, or 95 wt % or more, or 99 wt % or more) of the monomers used to form the polymer are monomers of formula (I) or (II) where R is an organic group that includes moieties selected from cyclic and aromatic moieties, each of which may optionally be halogenated. Most preferably, 100 wt % of the monomers used to form the polymer are monomers of formula (I) or (II) where R is an organic group that includes moieties selected from cyclic and aromatic moieties, each of which may optionally be halogenated.

It may be that some or all of the monomers used to form the polymer are monomers of formula (I) or (II) where R is an organic group that includes moieties selected from: phenyl, cycloalkyl, cycloalkenyl and heterocycloalkyl moieties, each of which may optionally be halogenated. Preferably 20 wt % or more (such as 25 wt % or more, 30 wt % or more, 33 wt % or more, or 40 wt % or more); more preferably 50 wt % or more (such as 55 wt % or more, 60 wt % or more, or 65 wt % or more); and most preferably 70 wt % or more (such as 75 wt % or more, 80 wt % or more, 85 wt % or more, or 90 wt % or more, or 95 wt % or more, or 99 wt % or more) of the monomers used to form the polymer are monomers of formula (I) or (II) where R is an organic group that includes moieties selected from: phenyl, cycloalkyl, cycloalkenyl and heterocycloalkyl moieties, each of which may optionally be halogenated. Most preferably, 100 wt % of the monomers used to form the polymer are monomers of formula (I) or (II) where R is an organic group that includes moieties selected from: phenyl, cycloalkyl, cycloalkenyl and heterocycloalkyl moieties, each of which may optionally be halogenated.

In one embodiment some or all of the monomers used to form the polymer are monomers of formula (I) or (II) where R is an organic group that includes moieties selected from: phenyl, cycloalkyl and cycloalkenyl moieties, each of which may optionally be halogenated. Preferably 20 wt % or more (such as 25 wt % or more, 30 wt % or more, 33 wt % or more, or 40 wt % or more); more preferably 50 wt % or more (such as 55 wt % or more, 60 wt % or more, or 65 wt % or more); and most preferably 70 wt % or more (such as 75 wt % or more, 80 wt % or more, 85 wt % or more, or 90 wt % or more, or 95 wt % or more, or 99 wt % or more) of the monomers used to form the polymer are monomers of formula (I) or (II) where R is an organic group that includes moieties selected from: phenyl, cycloalkyl and cycloalkenyl moieties, each of which may optionally be halogenated. Most preferably, 100 wt % of the monomers used to form the polymer are monomers of formula (I) or (II) where R is an organic group that includes moieties selected from: phenyl, cycloalkyl and cycloalkenyl moieties, each of which may optionally be halogenated.

In one embodiment some or all of the monomers used to form the polymer are monomers of formula (I) or (II) where R is an organic group that includes moieties selected from: phenyl and cycloalkyl moieties, each of which may optionally be halogenated. Preferably 20 wt % or more (such as 25 wt % or more, 30 wt % or more, 33 wt % or more, or 40 wt % or more); more preferably 50 wt % or more (such as 55 wt % or more, 60 wt % or more, or 65 wt % or more); and most preferably 70 wt % or more (such as 75 wt % or more, 80 wt % or more, 85 wt % or more, or 90 wt % or more, or 95 wt % or more, or 99 wt % or more) of the monomers used to form the polymer are monomers of formula (I) or (II) where R is an organic group that includes moieties selected from: phenyl and cycloalkyl moieties, each of which may optionally be halogenated. Most preferably, 100 wt % of the monomers used to form the polymer are monomers of formula (I) or (II) where R is an organic group that includes moieties selected from: phenyl and cycloalkyl moieties, each of which may optionally be halogenated.

In one embodiment some or all of the monomers used to form the polymer are monomers of formula (I) selected from the group (C):

Group (C)

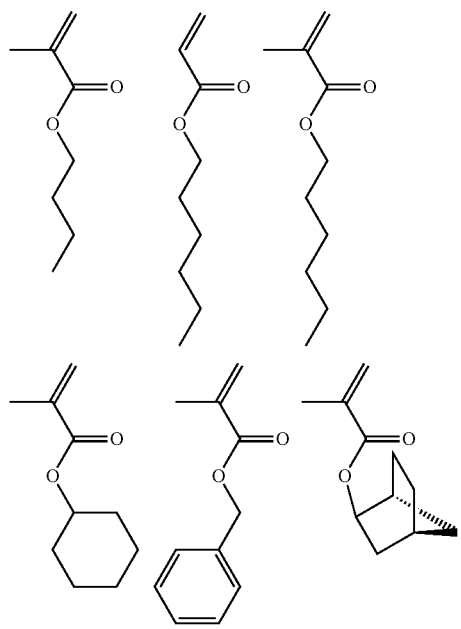

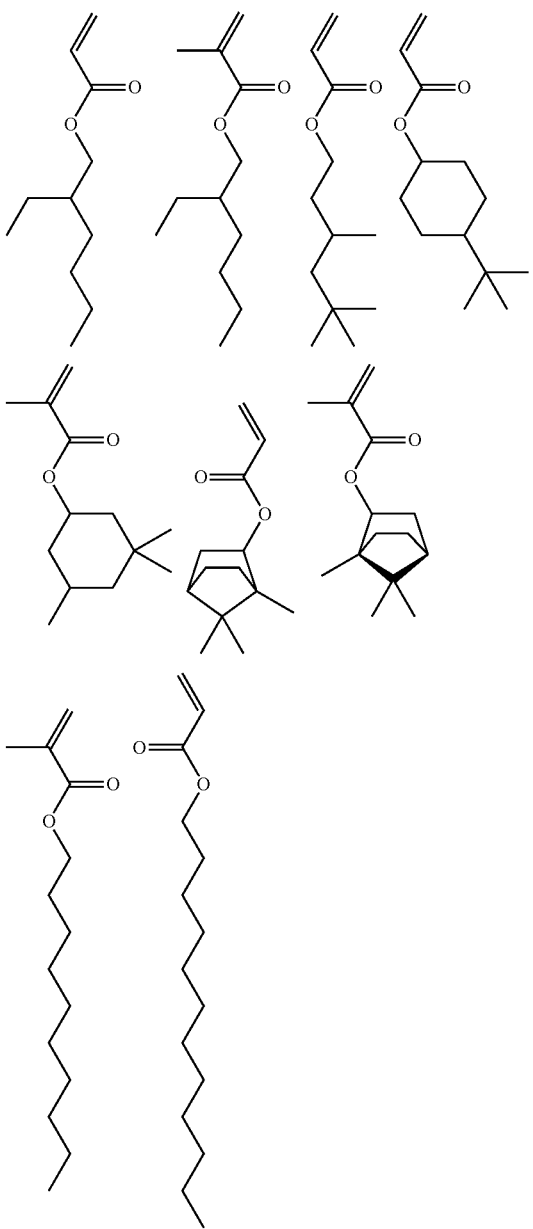

In one embodiment some or all of the monomers used to form the polymer are monomers of formula (I) selected from the group (D):

Group (D)

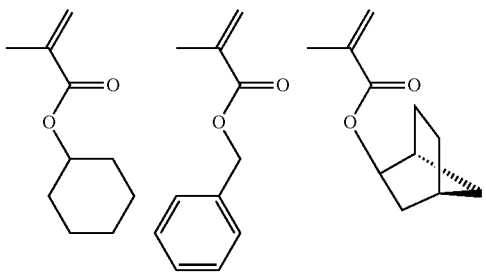

-continued

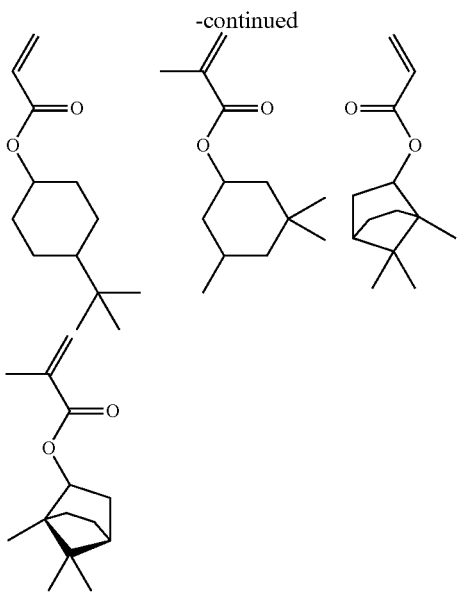

It may be that 20 wt % or more (such as 25 wt % or more, 30 wt % or more, 33 wt % or more, or 40 wt % or more); for example 50 wt % or more (such as 55 wt % or more, 60 wt % or more, or 65 wt % or more); e.g. 70 wt % or more (such as 75 wt % or more, 80 wt % or more, 85 wt % or more, or 90 wt % or more, or 95 wt % or more, or 99 wt % or more) of the monomers used to form the polymer are monomers of formula (I) selected from the group (C) (e.g. selected from the group (D)). In one embodiment, 100 wt % of the monomers used to form the polymer are monomers of formula (I) selected from the group (C) (e.g. selected from the group (D)).

The polymers described above have been found to have the beneficial effect of inhibiting bacterial attachment to a surface. Therefore they can be used in relation to surfaces of articles where it is desirable to avoid bacterial contamination and in particular to prevent or reduce biofilm formation.

The polymers may be used to inhibit bacterial attachment to a surface, and/or to prevent or reduce bacterial biofilm formation on a surface, in relation to any suitable bacteria. It may be that the bacteria are uropathogenic but other bacteria may also be relevant targets for the treatment.

The polymers may be used to inhibit bacterial attachment to a surface that is mediated by the mineralisation of salt components within urine.

The polymers may be used to prevent or reduce bacterial biofilm formation on a surface that is mediated by the mineralisation of salt components within urine.

The polymers may be used to inhibit bacterial attachment to a surface that is mediated by non-mineral components within urine, such as creatinine and urea.

The polymers may be used to prevent or reduce bacterial biofilm formation on a surface that is mediated by non-mineral components within urine, such as creatinine and urea.

The polymers may in one embodiment be used to inhibit bacterial attachment to a surface, where the bacteria comprise one or more bacteria within the genera *Streptococcus, Staphylococcus, Providencia, Morganella, Stenotrophomonas, Enterococcus, Yersinia, Salmonella, Serratia, Chlamydia, Coxilla, Ehrlichia, Francisella, Legionella, Pasteurella, Brucella, Proteus, Hilicobacter, Klebsiella, Enterobacter, Escherichia, Tropheryma, Acinetobacter, Aeromonas, Alcaligenes, Campylobacter, Capnocytophaga, Bacillus, Clostridium, Corynebacterium, Erysipelothrix, Listeria, Mycobacterium* and *Pseudomonas*.

In one such embodiment, the polymers may be used to inhibit bacterial attachment to a surface, where the bacteria comprise one or more bacteria selected from: *Staphylococcus aureus, Staphylococcus saprophyticus, Staphylococcus epidermidis, Escherichia coli, Pseudomonas aeruginosa, Proteus mirabilis, Providencia stuartii, Enterococcus faecalis, Proteus mirabilis, Klebsiella pneumoniae, Enterobacter aerogenes, Enterobacter cloacae, Serratia marcescens, Morganella morganii, Stenotrophomonas maltophilia, Clostridium difficile*, and other uropathogenic microorganisms.

The polymers may, for example, be used to inhibit bacterial attachment to a surface, where the bacteria comprise one or more of *Pseudomonas aeruginosa, Staphylococcus aureus* and *Escherichia coli*.

The polymers may also be used in another embodiment to prevent or reduce bacterial biofilm formation on a surface, where the bacteria comprise one or more bacteria within the genera *Streptococcus, Staphylococcus, Providencia, Morganella, Stenotrophomonas, Enterococcus, Yersinia, Salmonella, Serratia, Chlamydia, Coxilla, Ehrlichia, Francisella, Legionella, Pasteurella, Brucella, Proteus, Hilicobacter, Klebsiella, Enterobacter, Escherichia, Tropheryma, Acinetobacter, Aeromonas, Alcaligenes, Campylobacter, Capnocytophaga, Bacillus, Clostridium, Corynebacterium, Erysipelothrix, Listeria, Mycobacterium* and *Pseudomonas*.

In one such embodiment, the polymers may be used to prevent or reduce bacterial biofilm formation on a surface, where the bacteria comprise one or more bacteria selected from: *Staphylococcus aureus, Staphylococcus saprophyticus, Staphylococcus epidermidis, Escherichia coli, Pseudomonas aeruginosa, Proteus mirabilis, Providencia stuartii, Enterococcus faecalis, Proteus mirabilis, Klebsiella pneumoniae, Enterobacter aerogenes, Enterobacter cloacae, Serratia marcescens, Morganella morganii, Stenotrophomonas maltophilia, Clostridium difficile*, and other uropathogenic microorganisms.

The polymers may, for example, be used to prevent or reduce bacterial biofilm formation on a surface, where the bacteria comprise one or more of *Pseudomonas aeruginosa, Staphylococcus aureus* and *Escherichia coli*.

The invention also provides an article having a surface that is made of polymer, or that has a polymer coating.

Thus the polymer may be used to form all of the article, or the polymer may be used to form at least the part of the article comprising the surface, or the polymer may be used to coat the surface of the article. This may prevent or reduce biofilm formation on the surface.

The article may, for example, be related to any aspect of industry, home or garden. The article may be an article involved with medicine or surgery, food preparation, personal hygiene or water treatment.

The article may, in one embodiment, be a medical device such as a surgical instrument, or an implant or prosthesis, or a medical machine or component thereof.

In particular, the article may be selected from surgical instruments, such as forceps, reamers, pushers, pliers, or retractors; permanent implants, such as artificial heart valves, voice prostheses, prosthetic joints, implanted artificial lenses, stents (e.g. vascular stents), and shunts (e.g. hydrocephalus shunts); and non-permanent implants, such as pacemakers and pacemaker leads, drain tubes, endotracheal or gastrointestinal tubes, temporary or trial prosthetic joints, surgical pins, guidewires, surgical staples, cannulas, subcutaneous or transcutaneous ports, and indwelling catheters and catheter connectors, and contact lenses. The article may also be a medical machine or component thereof, for example, it may be selected from dialysis machines, dialysis water delivery systems, water circuits within a dialysis unit and water delivery systems for respirator therapy.

In one embodiment the article is a catheter. Examples of indwelling catheters include urinary catheters, vascular catheters (e.g. central venous catheters, dialysis catheters, peripheral venous catheters, arterial catheters and pulmonary artery Swan-Ganz catheters), peritoneal dialysis catheters, central venous catheters and needleless connectors.

The present invention allows the prevention of medical device-associated bacterial infections by providing the polymer that inhibits bacterial attachment on the surface of medical device products. For example, the polymers of the present invention offer the possibility to effectively reduce catheter-related bacterial infections.

The polymer can also be used to prevent or reduce the formation of biofilms in industrial settings, such as ship hulls, paper manufacturing, oil recovery plants, food processing plants, water processing plants, drinking water distribution systems, cooling towers and any other applications where biofouling on surfaces is a potential concern.

In one embodiment, the article is a component of process equipment, such as cooling equipment, water treatment equipment, or food processing equipment. In one such embodiment, the component is selected from: a cooling tower, a water treatment plant, a dairy processing plant, a food processing plant, a chemical process plant, and a pharmaceutical process plant.

It is also contemplated that the polymers are useful for coating onto food preparation surfaces, such as kitchen counters, cutting boards, sinks, stoves, refrigerator surfaces, or onto bathroom surfaces, such as toilets, sinks, bathtubs, showers, and drains. Other suitable treatable surfaces are floor surfaces, door surfaces and window surfaces.

In one embodiment, the article is a toilet bowl, a sink, a bathtub, a drain, a high-chair, a work surface, a food processing machine, a food preparation area, an air duct, or an air conditioning unit.

In one embodiment, the article is a component in a medical environment; preferably the article is a component in a hospital or a veterinary hospital.

The present invention has been shown to reduce bacterial attachment mediated by the mineralisation of salt components within urine. Therefore in one embodiment, the article is one that, in use, has a surface that contacts urine. For example it may be a toilet bowl, a chamber pot, a urinary catheter, a dialysis machine or a component of a dialysis machine. In one such embodiment the article is a medical device that includes a surface that, in use, contacts urine, especially a urinary catheter.

The invention also provides certain novel polymers. These are:
(i) homopolymers formed from a (meth) acrylate monomer selected from groups (A) and (B) as illustrated above; and
(ii) copolymers formed from (meth) acrylate monomers, wherein 70 wt % or more (e.g. 75 wt % or more) of the (meth) acrylate monomers are independently selected from groups (A) and (B) as illustrated above and all of the (meth) acrylate monomers are monomers of formula (I) as defined above.

The copolymers may therefore be formed entirely from (meth) acrylate monomers from groups (A) and (B) or it may be that 30 wt % or less (e.g. 28 wt % or less, such as from 1 to 25 wt %) of the monomers are of formula (I) but not from groups (A) and (B).

Co-monomers that are of formula (I) but that are not in group (A) or (B) include, but are not limited to, di(ethylene glycol) methyl ether methacrylate, ethylene glycol methyl ether methacrylate, ethylene glycol methyl ether acrylate and di(ethylene glycol) ethyl ether acrylate. Such co-monomers may, for example, be selected to achieve desired properties such as improved flexibility. For example, such co-monomers may be used to lower the polymer's glass transition temperature ($T_g$) to below room temperature.

In one embodiment the novel polymers are:
(i) homopolymers formed from a (meth) acrylate monomer or
(ii) copolymers formed from two (meth) acrylate monomers,
wherein the (meth) acrylate monomers are independently selected from the groups (A) and (B) as illustrated above.

In a preferred embodiment the monomers used to form the polymer are independently selected from monomers 4, 5, 8, 15 and B of group (A) and monomers 1', 2', 3', 4', 5', 6', 7', 8', 9', 10', 11', 12', 13', 15', 16' and 18' of group (B).

In one embodiment the monomers used to form the polymer are independently selected from monomers 6', 7', and 15' of group (B).

In one embodiment the novel polymer is a copolymer of two (meth) acrylate monomers. The two monomers may be used in any desired ratio, for example from 1:99 to 99:1, from 5:95 to 95:5, from 10:90 to 90:10, from 20:80 to 80:20, from 25:75 to 75:25, or from 30:70 to 70:30. In one embodiment the two monomers are used in a ratio from 33:67 to 67:33, e.g. from 1:2 to 2:1, for example the ratio may be 1:2, or 1:1, or 2:1.

In one embodiment the two (meth) acrylate monomers used to form the copolymer are each independently selected from: monomers 4, 5, 8 and B of Group A and monomers 1', 2', 3', 4', 5', 6', 7', 8', 9', 10', 11', 12', 13', 15', 16' and 18' of group (B).

In one embodiment the (meth) acrylate monomers used to form the copolymer include at least one monomer selected from monomers 6', 7' and 15' of Group B. In one embodiment monomer 7' of Group B is one of the (meth) acrylate monomers used to form the copolymer. It may be that the copolymer comprises 50% wt or more of monomer 7' of Group B, such as 60% or more, 70% or more or 80% or more, e.g. from 70 to 99% or from 75 to 95%. In one embodiment the copolymer is formed from monomer 7' and monomer 6' of Group B; optionally the ratio of 7' to 6' may be from 10:90 to 90:10, such as from 70:30 to 90:10, e.g. from 75:25 to 80:20.

In one embodiment, the copolymer is selected from the group consisting of:
copolymers of monomer B of group (A) with monomer 4 of group (A).
copolymers of monomer B of group (A) with monomer 5 of group (A).
copolymers of monomer B of group (A) with monomer 8 of group (A).
copolymers of monomer 18' of group (B) with monomer 8' of group (B).
copolymers of monomer 7' of group (B) with monomer 8' of group (B).
copolymers of monomer 4' of group (B) with monomer 12' of group (B).
copolymers of monomer 2' of group (B) with monomer 8' of group (B).

copolymers of monomer 3' of group (B) with monomer 2' of group (B).

copolymers of monomer 6' of group (B) with monomer 7' of group (B).

copolymers of monomer 10' of group (B) with monomer 13' of group (B).

copolymers of monomer 4' of group (B) with monomer 11' of group (B).

copolymers of monomer 7' of group (B) with monomer 13' of group (B).

copolymers of monomer 4' of group (B) with monomer 15' of group (B).

copolymers of monomer 2' of group (B) with monomer 15' of group (B).

copolymers of monomer 7' of group (B) with monomer 1' of group (B).

copolymers of monomer 7' of group (B) with monomer 5' of group (B).

copolymers of monomer 10' of group (B) with monomer 9' of group (B).

copolymers of monomer 2' of group (B) with monomer 5' of group (B).

copolymers of monomer 12' of group (B) with monomer 3' of group (B).

copolymers of monomer 7' of group (B) with monomer 10' of group (B).

copolymers of monomer 7' of group (B) with monomer 16' of group (B).

copolymers of monomer 15' of group (B) with monomer 13' of group (B).

Other novel polymers are (i) homopolymers formed from a (meth) acrylate monomer selected from group (C); and (ii) copolymers formed from (meth) acrylate monomers, wherein 70 wt % or more (e.g. 75 wt % or more) of the (meth) acrylate monomers are independently selected from group (C) as illustrated above.

The copolymers may therefore be formed entirely from (meth) acrylate monomers from group (C) or it may be that 30 wt % or less (e.g. 28 wt % or less, such as from 1 to 25 wt %) of the monomers are of formula (I) but not from group (C).

Co-monomers that are of formula (I) but that are not in group (C) include, but are not limited to, di(ethylene glycol) methyl ether methacrylate, ethylene glycol methyl ether methacrylate, ethylene glycol methyl ether acrylate and di(ethylene glycol) ethyl ether acrylate. Such co-monomers may, for example, be selected to achieve desired properties such as improved flexibility. For example, such co-monomers may be used to lower the polymer's glass transition temperature ($T_g$) to below room temperature.

In one embodiment the novel polymers are (i) homopolymers formed from a (meth) acrylate monomer selected from group (C); and (ii) copolymers formed from two (meth) acrylate monomers, wherein the (meth) acrylate monomers are each independently selected from group (C).

In one embodiment the (meth) acrylate monomers are each independently selected from group (D) as illustrated above.

In one embodiment the novel polymer is a copolymer of two (meth) acrylate monomers. The two monomers may be used in any desired ratio, for example from 1:99 to 99:1, from 5:95 to 95:5, from 10:90 to 90:10, from 20:80 to 80:20, from 25:75 to 75:25, or from 30:70 to 70:30. In one embodiment the two monomers are used in a ratio from 33:67 to 67:33, e.g. from 1:2 to 2:1, for example the ratio may be 1:2, or 1:1, or 2:1.

The novel polymers may suitably be formed by photo polymerisation of the monomers. However, other known polymerisation techniques may also be contemplated. Polymerisation of (meth) acrylate monomers is known in the art.

The invention will now be further described, in a non-limiting manner, with reference to the Examples.

EXAMPLES

Example 1

Summary

Sixteen monomers (monomers 1-16 as shown in FIG. 1), were mixed as the major component with another six monomers (monomers A-F as shown in FIG. 1) at ratios of 100:0, 90:10, 85:15, 80:20, 75:25 and 70:30 to create 496 unique monomer solutions. This provided a material library for micro array covering a large combinatorial space. These solutions were printed in triplicate as 300 µm diameter spots onto a poly(hydroxyl ethylmethacrylate) (pHEMA) coated microscope slide and photopolymerised.

To develop a high throughput bacterial adherence assay, three pathogens PA01, 8325-4 and UPEC were transformed with plasmids with a green fluorescent protein (GFP) gene, and subsequently incubated with the polymer microarray for 72 hours. The attachment was quantified to determine the fluorescence signal ($F$) from each strain using a high throughput fluorescence approach. The value of $F$ from each strain on each material composition was normalised to the maximum intensity on each slide and averaged over all three replicates on the slide to produce a bacterial performance value ($\tau$) that weights its relative resistance to each strain equally. The defined RPMI-1640 medium was used as it does not contain protein and, thus, bacterial-material interactions could be directly studied without interference from protein-mediated surface interactions.

A shortlist of five monomers was selected and a second generation array was designed by mixing these monomers with each other at ratios of 100:0, 90:10, 85:15, 80:20, 75:25, 70:30, 60:40, 55:45, 45:55, 40:60, 30:70, 25:75, 20:80, 15:85 and 10:90. The resultant array contained 150 materials including 5 materials as positive controls.

From the second generation array the top 6 compositions with low bacterial attachment and biofilm formation were chosen for scale up. Surface characterisation was applied to assess the physical and chemical similarities between the micro and macro polymer spots.

The scaled up materials were incubated with each of the three bacterial strains (*P. aeruginosa, S. aureus* and *E. coli* were used as representative pathogens) for 72 hours and the bacterial coverage was determined by staining the cells with SYTO17 and confocal microscopy.

Methods

Polymer Array Synthesis.

Polymer micro arrays were synthesised using the methods previously described in Anderson D G et al (2004) Nature Biotechnology 22(7):863-866. Monomers were purchased from Aldrich, Scientific Polymers and Polysciences and printed onto epoxy-coated slides (Xenopore) dip-coated into 4% (w/v) pHEMA (Aldrich). The arrays were dried at <50 mTorr for at least 7 days.

High Throughput Surface Characterisation.

Arrays were characterised by AFM, WCA, XPS and ToF-SIMS.

ToF SIMS measurements were conducted on an ION-ToF IV instrument operated using a monoisotopic Ga⁺ primary ion source operated at 25 kV and in "bunched mode". A 1 pA primary ion beam was rastered, and both positive and negative secondary ions were collected from a 100×100 μm area of each polymer spot in the microarray over 10-second acquisition time. Ion masses were determined using a high resolution Time-of-Flight analyser allowing accurate mass assignment. The typical mass resolution (at m/z 41) was just over 6000. XPS was carried out on a Kratos Axis Ultra instrument using monochromated Al Kα radiation (1486.6 eV), 15 mA emission current, 10 kV anode potential and a charge-compensating electron flood. High-resolution core levels were acquired at a pass energy of 20 eV. WCA were measured using the sessile drop method on a fully automated Krüss DSA 100 instrument. A water drop with a volume of ~400 picoliter was used.

AFM measurements were taken using a Nanoscope 3000A instrument in tapping mode. Silicon tips with a resonant frequency of approximately 300 kHz and a force constant of 40 N/m were used (Tap300A1, Budget Sensors) for dry state and silicon nitride tips with a resonant frequency of 7.5 kHz were used for fluid measurements. 5 μm regions of the polymer were taken and the root mean square (RMS) roughness was measured across this region.

The ToF SIMS spectra data were analysed using principle component analysis (PCA), and the correlation between ToF SIMS spectra and bacterial attachment was analysed using partial least squares (PLS) regression. Both multivariate analysis methods were carried out using the Eigenvector PLS_Toolbox 3.5.

Scale Up of Materials.

Selected compositions were scaled up to 6 mm polymer discs. These were prepared by casting 5 μLs of monomer solution (75% (v/v) monomer, 25% (v/v) DMF and 1% (w/v) 2,2-dimethoxy-2-phenyl acetophenone) onto epoxy-functionalised slides (Xenopore) dip-coated into 4% (w/v) pHEMA. Samples were irradiated with a long wave UV source for 10 mins to initiate polymerisation. The $O_2$ content was maintained below 2000 ppm for the duration of the process. The samples were then dried at <50 mTorr for at least 7 days. 4 cm long silicone catheters (Bard) were cut from a native catheter (7.3 mm outer diameter). The inside and outside surfaces were oxygen plasma treated for one minute at 50 W. The plasma treated catheters were immediately immersed in monomer solution for 10 s and blotted to remove excessive monomer solution before photopolymerisation using UV (365 nm) for one minute. The $O_2$ content was maintained below 2000 ppm for the duration of the process. The samples were then maintained at <50 mTorr for at least 7 days.

Bacterial Culture.

Three bacterial strains, *P. aeruginosa* PAO1, *S. aureus* 8325-4 and *E. coli* (UPEC) were routinely grown on either LB (Luria-Bertani, Oxoid, UK) agar plates at 37° C. or in broth at 37° C. with 200 rpm shaking. Three constitutively GFP-expressing plasmids, pGFP, pSB2019 and pSB2020 (25) were transformed into PAO1, *S. aureus* and UPEC respectively and maintained in the bacterial cells by adding appropriate antibiotics to the culture media.

Before starting the attachment/biofilm assay, the slides were washed in distilled $H_2O$ for 10 min and air-dried. Bacteria were grown on the polymer slides under similar conditions to those previously described in Diggle S P et al (2006) Environmental Microbiology 8(6):1095-1104 and Johansson E M V et al (2008) Chemistry & Biology 15(12): 1249-1257. Briefly, UV-sterilized polymer slides were incubated in 15 ml RPMI-1640 medium (Sigma, UK) or artificial urine (AU) inoculated with GFP-tagged bacteria (from overnight cultures diluted to an $OD_{600}$ 0.01) at 37° C. with 60 rpm shaking for 24 hours or 72 hours. In order to test any bacteria-material interactions mediated by components within urine such as the precipitation of salt, some slides were conditioned with AU by an incubation with AU for 72 hour at 37° C. with 3 subsequent washes for 5 minutes in RMPI-1640 prior to inoculation with bacteria. The composition of AU was the same as previously reported in Brooks T et al, Letters in Applied Microbiology, 24: 203-206. The slides in medium without bacteria were also set up for medium control. At the desired time points, the slides were removed from bacterial culture and washed with 15 ml phosphate buffered saline (PBS, Oxoid, UK) at room temperature for 5 minutes three times. After rinsing with distilled $H_2O$ to remove salt and air dried, the fluorescent images from the slides in medium only and medium containing bacteria were acquired using a GenePix Autoloader 4200AL Scanner (Molecular Devices, US) with a 488 nm excitation laser and standard blue emission filter (510-560 nm). The total fluorescent intensities from polymer spots were acquired using GenePix Pro 6 software (Molecular Devices, US).

The fluorescence signal (F) from each bacterial strain was determined using equation 1 where F is the fluorescence intensity measured per unit area by the laser scanner after incubation with bacteria and $F_{control}$ is the fluorescence intensity measured per unit area by the laser scanner measured on a control slide consisting of a replica array that was incubated in media for 72 hours without bacteria.

$$\mathcal{F} = F - F_{control} \qquad \text{(Equation 1)}$$

The bacterial performance (τ) was determined using equation 2 where the subscript to the F indicates the bacterial strain and the $F_{max}$ is the maximum fluorescence signal measured on any spot on the array for a given strain.

$$\tau = \left( \frac{F_{PAO1}}{F_{PAO1max}} + \frac{F_{8325}}{F_{8325max}} + \frac{F_{UPEC}}{F_{UPECmax}} + \frac{F_{UPECinAU}}{F_{UPECinAUmax}} + \frac{F_{UPECAUconditioned}}{F_{UPECAUconditioned\,max}} \right) \div 5 \times 100 \qquad \text{(Equation 2)}$$

Results and Comment

First Generation Array—Surface Characterisation of Materials

X-ray photoelectron spectroscopy (XPS), atomic force microscopy (AFM), time of flight secondary ion mass spectrometry (ToF SIMS), and water contact angle (WCA) measurement were used to characterise each polymer sample on the array. The influence of each property on bacterial attachment was assessed for all three pathogens separately. No correlation was identified between bacterial attachment and elemental composition, WCA or roughness across all 496 materials studied.

ToF SIMS analysis coupled with PLS was applied to search for correlations between the surface chemistry of the array and the τ from each strain.

Figure 2:
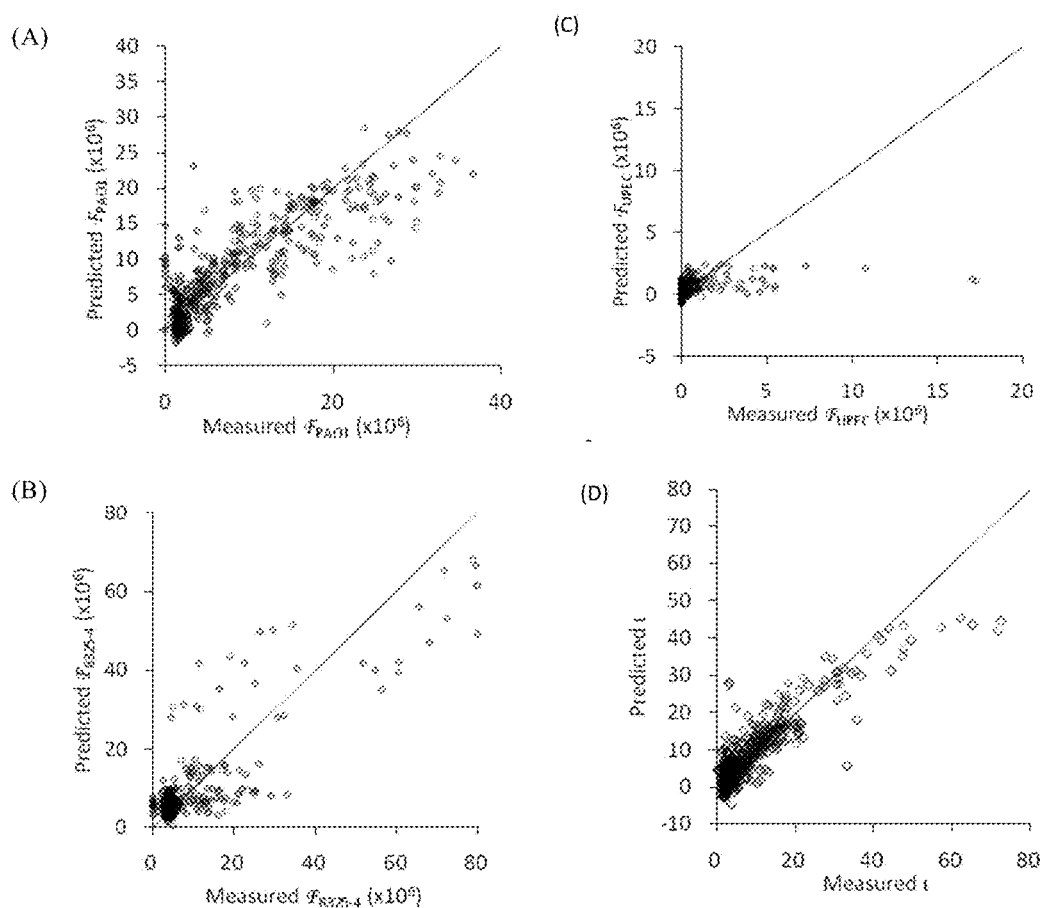
FIG. 2 shows plots for predicted bacterial attachment, as determined from a model generated by ToF-SIMS and PLS analysis, against the experimentally determined value after 72 hour incubation of the polymer array in Example 1.

The results are shown in FIG. 2. In this regard, a plot of the predicted bacterial attachment determined from the model generated by ToF-SIMS and PLS analysis against the experimentally determined value after 72 hour incubation of the polymer array is shown in (A) for PA01 ($R^2$=0.71), in (B)

for *S. aureus* 8325-4 ($R^2$=0.74), in (C) for UPEC($R^2$=0.6) and in (D) for τ ($R^2$=0.87) in RPMI. The y=x line is drawn as a guide The PLS model produced by this analysis was therefore able to identify correlations between the $\bar{r}$ and the ToF-SIMS spectra, with an $R^2$ value of 0.71 and 0.74 for PAO1 and *S. aureus*, respectively.

The successful prediction of bacterial attachment of PAO1 and *S. aureus* demonstrates the surface chemical dependence of attachment of these strains. Furthermore, PLS regression was able to predict the τ value for each material with an $R^2$ value of 0.87. This result suggests that there are some common chemical functionalities that determine bacterial attachment and subsequent biofilm formation across all three strains.

The PLS model generates a regression coefficient for each secondary ion (fragment) whereupon the regression coefficient indicates the degree of influence of each secondary ion on bacterial attachment and biofilm formation; positive coefficients indicate that the ion in question promote whilst negative ones resist bacterial attachment and biofilm formation. Surface chemical moieties that strongly (reflected by the absolute value of the regression coefficient) resisted bacterial attachment and biofilm formation for both the PAO1 and *S. aureus* strains were identified.

FIG. 3 shows the key ions identified by ToF-SIMS analysis combined with PLS analysis as important for bacterial attachment to surfaces for both PAO1 and *S. aureus*.

In general, hydrocarbon ions are correlated with low bacterial attachment. In particular, cyclic carbon groups from polymer 4 and B ($C_2H^-$, $C_6H^-$, $C_4H^-$), ester groups from polymer 15 and 13 ($CHO_2^-$), tertiary butyl group from polymer 5 ($C_4H_7^+$), and hydrocarbon pendant group from polymer 2, 8 and 12 ($C_2H_3^+$, $C_3H_3^+$, $C_4H_5^+$, $C_2H_5^+$, $C_3H_7^+$) were correlated with low bacterial attachment.

Meanwhile, oxygen containing ions are correlated with higher bacterial attachment. For example, the hydroxyl group containing fragment in monomer 10 ($C_4H_5O_2^-$, $C_6H_{11}O_3^-$), correlated positively with bacterial attachment.

Second Generation Array

The second generation array mixed five monomers from the first generation array (4, 5, 8, 15, B) with each other at ratios of 100:0, 90:10, 85:15, 80:20, 75:25, 70:30, 60:40, 55:45, 45:55, 40:60, 30:70, 25:75, 20:80, 15:85 and 10:90. The resultant array contained 149 materials including 4 materials as positive controls (selected as the materials having the most bacterial attachment across the 3 strains from the first generation array). Bacterial attachment was assessed on the array for all three strains at 72 hours and the τ value for each material was determined.

Figure 4:
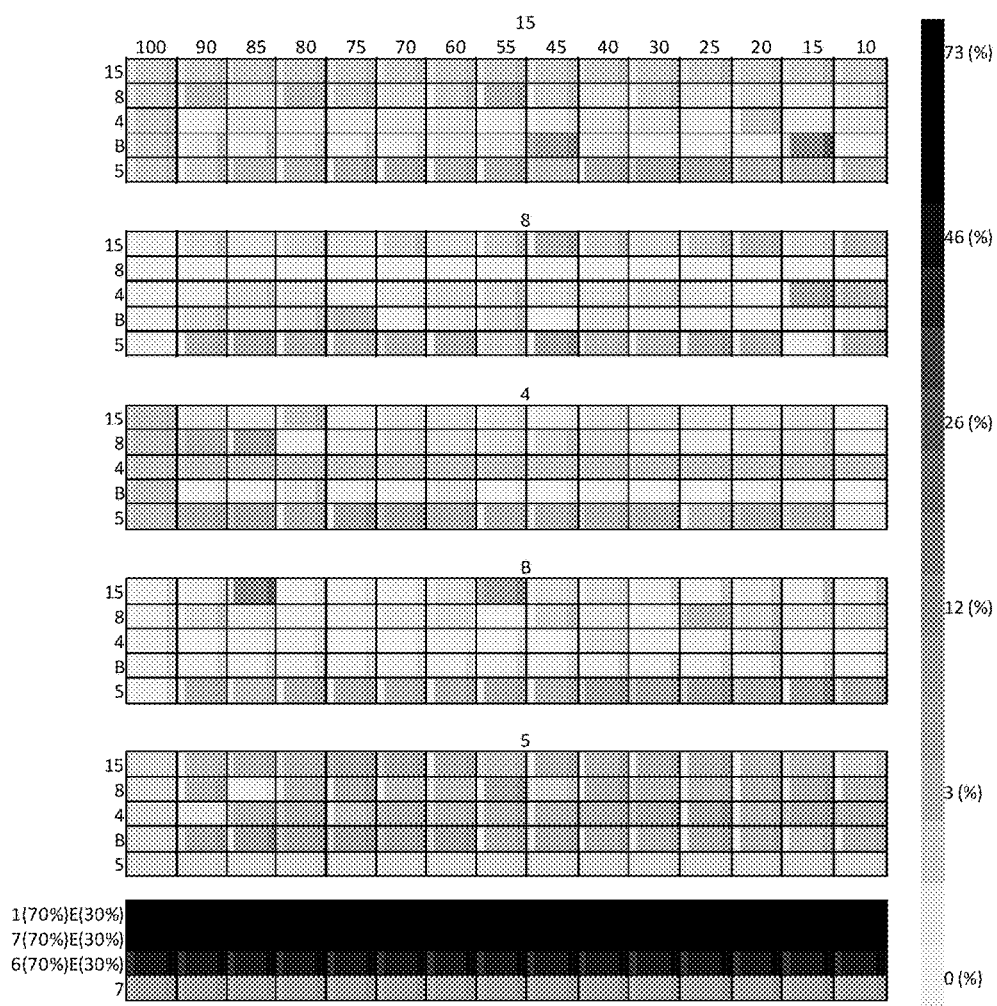
FIG. 4 shows the determined t values for each material as represented in the second generation array of Example 1.

The results for τ determined for all materials represented in the second generation array are shown in FIG. 4.

The numbers across the x-axis indicate the percentage composition of the monomers indicated above each block of samples, and the remainder of the solution is made up by the monomer indicated in the y-axis.

Copolymers of monomer B showed the greatest resistance to bacterial attachment, particularly when polymerised with monomer 5. The resultant copolymers performed better than the homopolymers, with the homopolymers of B and 5 having τ values of 0.32% and 0.51, respectively, compared with the copolymers of B and 5 with ratios of 40:60 and 45:55 (B:5) that both had τ values of 0% ($\bar{r}$ below limit of detection (LOD) for all three strains). This demonstrates the synergistic effects that can occur when forming copolymers and the importance of screening for copolymers by the methodology described.

The test materials based on monomers 4, 5, 8, 15 and B all resisted bacterial attachment mediated by the mineralisation of salt components within urine.

Scale Up

The compositions scaled up were 4(100%), 5(100%), 8(100%), B(100%), B(70%)5(30%), B(90%)4(10%), B(60%)4(40%), B(60%)8(40%), 8(75%)B(25%) and 4(60%)B(40%). For selection, where material composition only differed by 5% only one of the materials was chosen in order to increase the chemical diversity of materials scaled up. Materials were scaled up both to a 10 mm coupon and as a coating on a silicone catheter.

Initial scale up of monomer 15 (and other triacrylates) resulted in brittle materials that frequently cracked, thus, this material was removed from subsequent scale up experiments.

Surface characterisation was applied to assess the physical and chemical similarities between the micro and macro polymer spots. The WCA of scaled-up materials agreed well with those measured from materials in a microarray for all compositions. Furthermore, PCA analysis of the ToF-SIMS spectra of the scaled up and arrayed materials demonstrate a very close chemical similarity between arrayed and scaled up materials of 8(100%) and B (90%)4(10%), where the PCA analysis was unable to separate these materials when considering 84% of the variance in the set of materials.

To assess the similarity of the surface roughness AFM images were taken of the materials on the array and samples scaled up. The roughness values for both sample sets were similar with values for all samples between 0.5 and 0.95 nm measured. No phase separation was observed for the 6 scaled up copolymers.

Screening

The utility of the optimal compositions for a biomedical device was shown by incubating the scale up materials with each of the three bacterial strains for 72 hours and the bacterial coverage was determined by staining the cells with SYTO17 and confocal microscopy.

Figure 5:
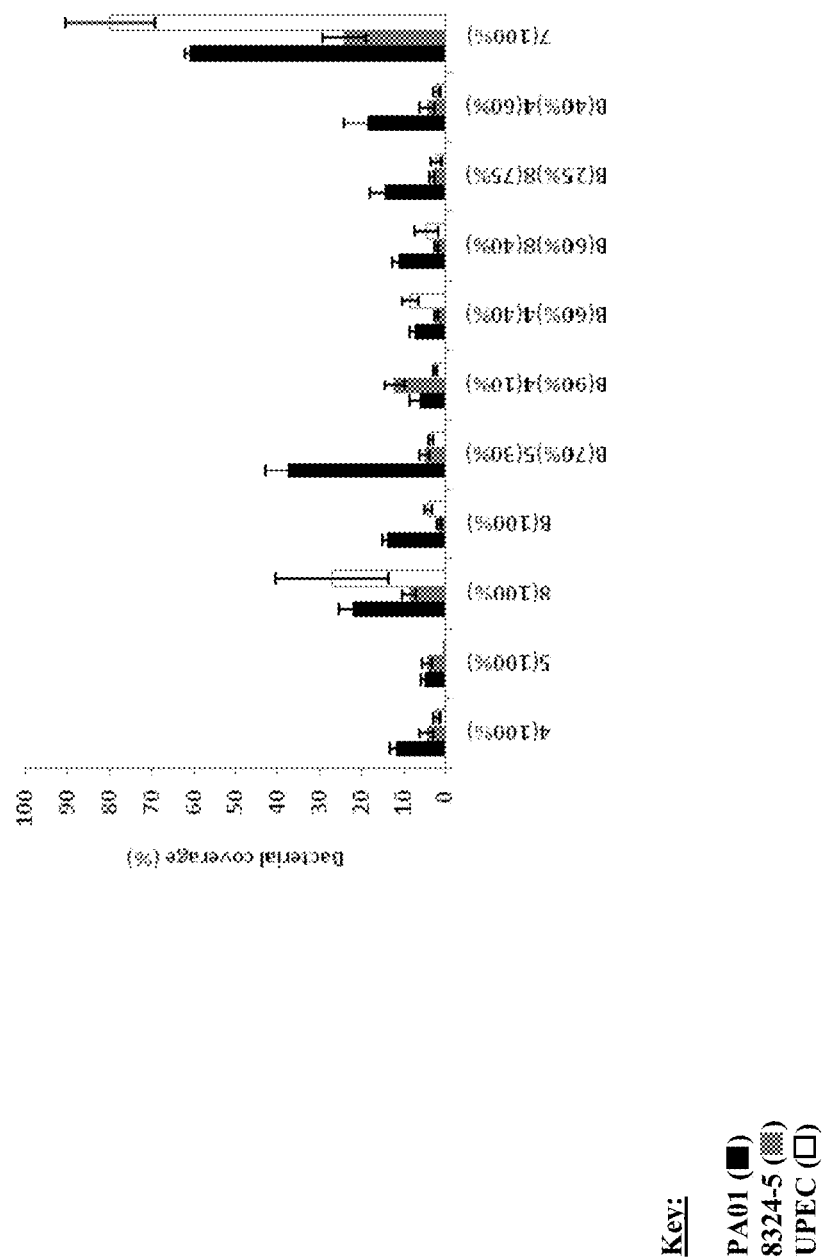
FIG. 5 shows the biological performance of ten scaled up materials, tested as 10 mm coupons in Example 1, as determined by incubating the materials with each of the three bacterial strains PAO1, *S. aureus* and UPEC for 72 hours. The homopolymer of 7 was used as a positive control.

FIG. 5 shows the biological performance of the scaled up materials as 10 mm coupons. The bacterial coverage as measured on the 10 scaled-up materials after 72 hour incubation is shown for PAO1 (■), *S. aureus* (▨) and UPEC (□) in RPMI-1640. The homopolymer of 7 was used as a positive control.

This study again showed synergistic effects of copolymer materials. For example the homopolymer of 8 had bacterial coverage for PAO1, *S. aureus* and UPEC of 21%, 9% and 27% respectively, however, when mixed with monomer B the coverage decreased to 11%, 4% and 3% respectively, which is also lower than the coverage measured on the homopolymer of B for the PAO1 and UPEC strains, which gave coverage of 14% and 4% respectively.

Overall, the two materials with the lowest bacterial coverage were the homopolymer of 5, with bacterial coverage for PAO1, *S. aureus* and UPEC of 5%, 4% and 0.4% respectively, and B(60%)4(40%) with bacterial coverage for PA01, 8325-4 and UPEC of 7%, 2% and 8%, respectively.

Figure 6:
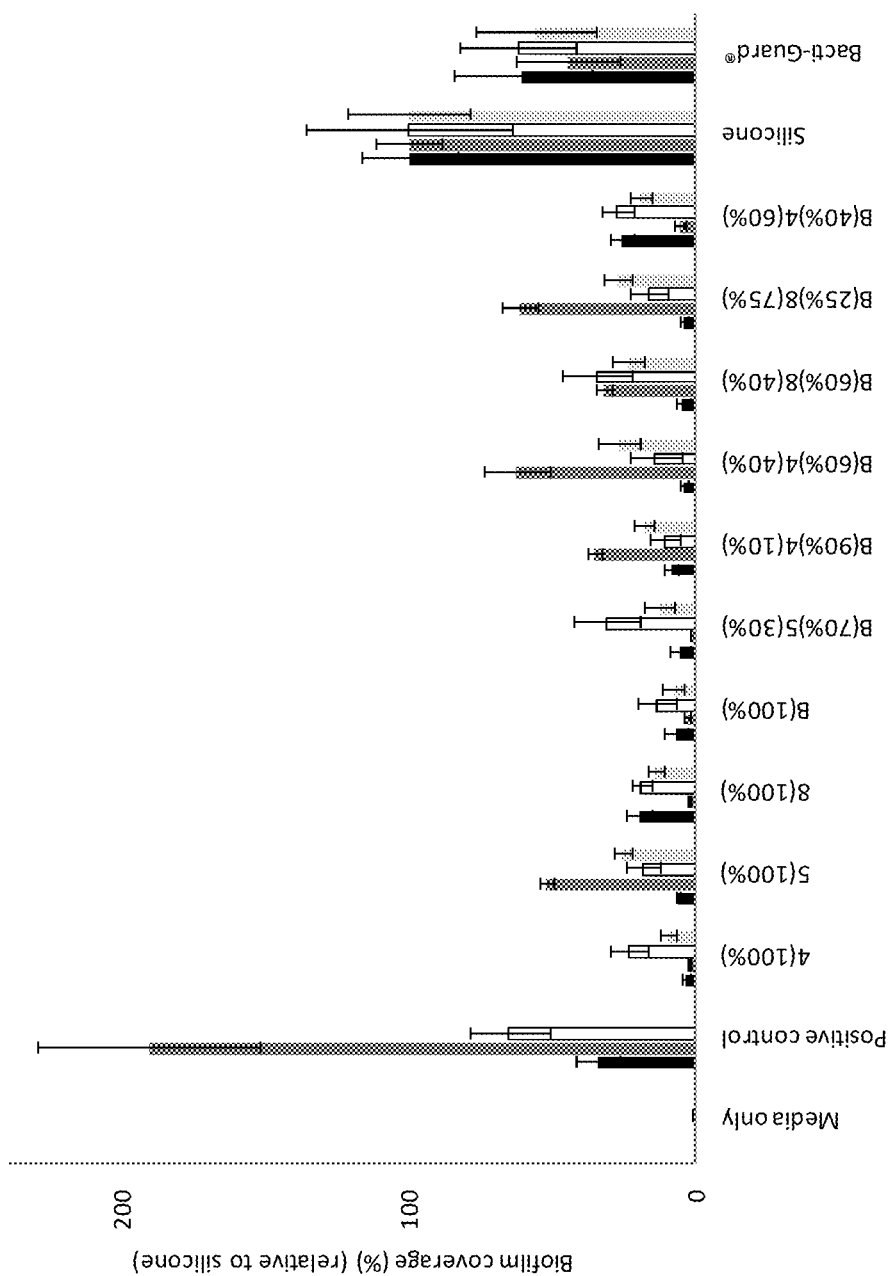
FIG. 6 shows the bacterial performance of ten scaled up materials, tested as coatings on a silicone catheter in Example 1, as determined by quantification of bacterial coverage for *P. aeruginosa, S. aureus*, UPEC and i from confocal images taken of 5 areas on each sample. Coverage was normalized to the coverage on bare silicone. The error bars equal one standard deviation unit: n=5.

FIG. 6 shows the bacterial performance of the scaled up materials as coatings on a silicone catheter. This was achieved by quantification of bacterial coverage for *P. aeruginosa* (■), *S. aureus* (▨), UPEC (□) and i (▧) from confocal images taken of 5 areas on each sample. Coverage was normalized to the coverage on bare silicone. The error bars equal one standard deviation unit: n=5. The composition of the positive control was specific to the pathogen used: *P. aeruginosa*=6(100%), *S. aureus*=7(100%), UPEC=1(70%)E(30%).

In all cases the coated catheters had lower biofilm coverage than the uncoated silicone, which had biofilm coverage of 32.6±5.5%, 33.4±3.9%, and 10.9±3.9% for *P. aeruginosa*, *S. aureus* and UPEC, respectively, and the silver embedded Bardex® coated BactiGuard® catheter that had biofilm coverage of 19.7±7.7%, 15.0±6.0%, and 6.8±2.2% for *P. aeruginosa*, *S. aureus* and UPEC, respectively. In comparison, the lowest biofilm coverage for *P. aeruginosa*, *S. aureus* and UPEC was the homopolymer of 4 with a biofilm coverage of 1.2±0.5% (60 fold reduction), the copolymer of monomers B:5 (70:30) with a biofilm coverage of 0.5±0.3% (110 fold reduction), and the copolymer of B:4 (90:10) with a biofilm coverage of 1.2±0.6% (50 fold reduction), respectively. The homopolymer of B produced the catheter coating with the lowest i value of 7.8±4.0%, hence preventing biofilm formation for a wide spectrum of bacteria. The coverage for each bacteria measured on this coating was 2.3±1.3%, 1.0±0.4%, and 1.5±0.7% for *P. aeruginosa*, *S. aureus* and UPEC, respectively. This amounted to a 12-fold reduction in biofilm coverage compared with an uncoated silicone catheter and a 7-fold reduction compared with the silver embedded Bardex® coated BactiGuard® catheter (i=55.8±20.9%).

Example 2

Summary

A first generation array of 116 acrylate and methacrylate homopolymers was screened for antibacterial properties. From this array 18 monomers were selected that produced homopolymers that had less bacterial attachment that the pHEMA background. These monomers were mixed together pairwise to produce a second generation array of 324 copolymers that were screened for antibacterial properties.
Methods
Monomers Initially an array of 116 acrylate and methacrylate homopolymers was screened for antibacterial properties. The 116 homopolymers was produced from monomers commercially available from Sigma that were amenable to the polymer microarray format.

A range of responses to bacteria were observed ranging from low to high bacteria adherence. From this array 18 monomers were selected that produced homopolymers that had less bacterial attachment that the pHEMA background.
Substrate Formation Epoxy coated glass slides (Genetix) were dip-coated with a pHEMA solution. The pHEMA solution was prepared by dissolving pHEMA (Sigma, cell culture tested) in 95% ethanol in a 50 mL centrifuge tube. For dissolution, the flask was vortexed for 30 mins. For dip-coating, in a laminar flow hood slides were rapidly dipped into the pHEMA solution, and withdrawn at a rate of 15 mm/s. Slides were then inverted and then maintained in a vertical position on a paper towel for at least 10 min to allow for drainage before being placed into a slide rack and placed in a vacuum oven for 1 hour.
Polymer Microarray Formation Polymer microarrays were formed using a contact printer (c) (Biodot). Printing conditions were $O_2$<1300 ppm, 25° C., 30% humidity. Slotted metal pins (946MP6B, Arrayit) with a diameter of 220 μm were used to transfer approximately 2.4 nL of monomer solution onto 10 substrates before slides were irradiated with a long wave UV source for 30 s.

Polymerisation solution was composed of 75% (v/v) monomer in DMF with 1% (w/w) photoinitiator 2,2-dimethoxy-2-phenylacetophenone. The argon atmosphere was achieved by purging the system with argon at a flow rate of 35 L/min. Once formed arrays were dried at <50 mTorr for 7 days. For all arrays the region on the glass slide with no pHEMA coating was kept to the right.
Bacterial Growth Three different bacterial species, *P. aeruginosa*, PAO1, *S. aureus* 8325-4 and *E. coli* UPEC were routinely grown on either LB (Luria-Bertani, Oxoid, UK) agar plates at 37° C. or in broth at 37° C. with 200 rpm shaking. Three constitutively GFP expressing plasmids, pGFP, pSB2019 and pSB2020 were transformed into *P. aeruginosa* PAO1, *S. aureus* 8325-4, and *E. coli* UPEC respectively and maintained by adding appropriate antibiotics to the culture media.

Prior to incubation with the bacteria, the microarray slides were washed in distilled $H_2O$ for 10 min and air-dried. UV-sterilized polymer slides were incubated in 15 ml RPMI-1640 defined medium (Sigma, UK) or artificial urine (AU) inoculated with diluted ($OD_{600}$=0.01) GFP-tagged bacteria from overnight cultures grown at 37° C. with 60 rpm shaking for 24 h or 72 h. In order to test any bacteria-material interactions mediated by components within urine, such as the precipitation of salt, some slides were conditioned with AU by an incubation with AU for 72 hours at 37° C. with 3 subsequent washes for 5 minutes in RMPI-1640 prior to inoculation with bacteria. The composition of AU was the same as previously reported in Brooks T et al (1997), Letters in Applied Microbiology, 24: 203-206. As growth medium controls, the slides were also incubated RPMI-1640 without bacteria. At the desired time points, the slides were removed, and washed three times with 15 ml phosphate buffered saline (PBS, Oxoid, UK) at room temperature for 5 min. After rinsing with distilled $H_2O$ to remove salts and air dried, the fluorescent images from the slides incubated medium only and medium containing bacteria were acquired using a GenePix Autoloader 4200AL Scanner (Molecular Devices, US) with a 488 nm excitation laser and standard blue emission filter (510-560 nm). The total fluorescence intensity from polymer spots were acquired using GenePix Pro 6 software (Molecular Devices, US).

The fluorescence signal (F) from each bacterial strain was determined using equation 1 where F is the fluorescence intensity measured per unit area by the laser scanner after incubation with bacteria and $F_{control}$ is the fluorescence intensity measured per unit area by the laser scanner measured on a control slide consisting of a replica array that was incubated in media for 72 h without bacteria.

$$F = F - F_{control} \quad \text{(Equation 1)}$$

The bacterial performance (τ) was determined using equation 2 where the subscript to the F indicates the bacterial strain and the $F_{max}$ is the maximum fluorescence signal measured on any spot on the array for a given strain.

$$\tau = \left( \frac{F_{PAO1}}{F_{PAO1max}} + \frac{F_{8325}}{F_{8325max}} + \frac{F_{UPEC}}{F_{UPECmax}} + \frac{F_{UPECinAU}}{F_{UPECinAUmax}} + \frac{F_{UPECAUconditioned}}{F_{UPECAUconditioned\,max}} \right) \div 5 \times 100 \quad \text{(Equation 2)}$$

Results

Figure 7:
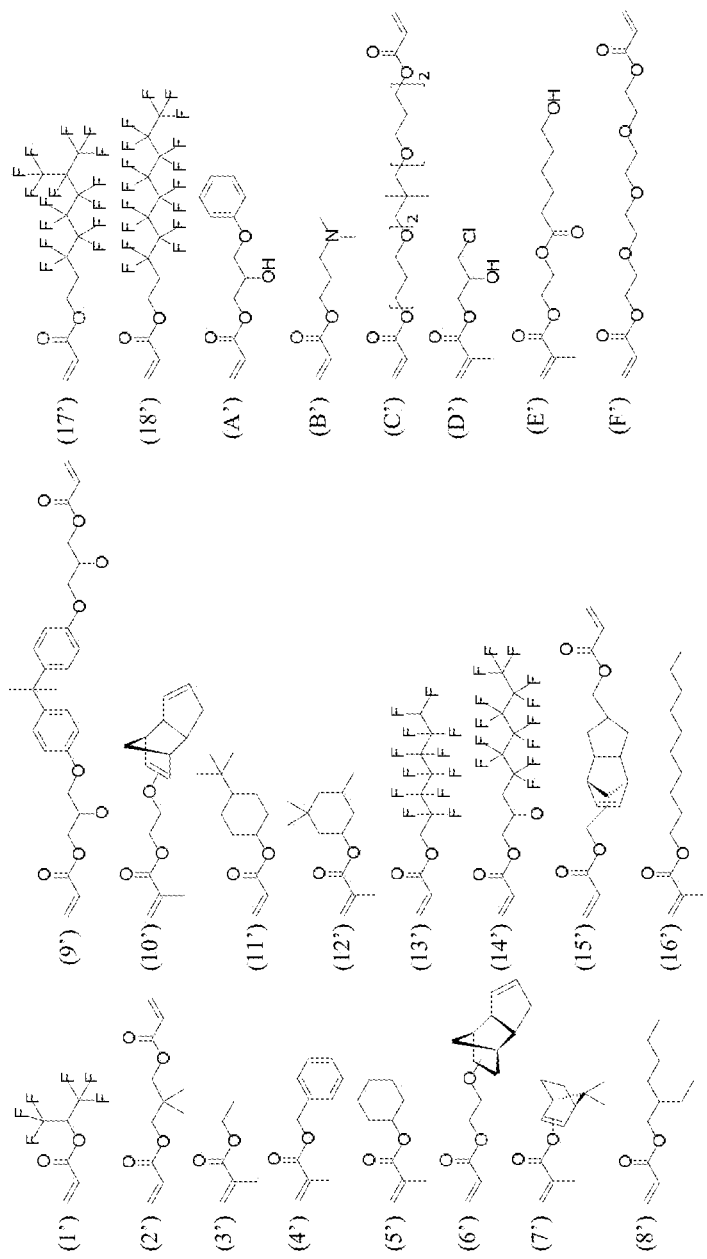
FIG. 7 shows the monomers 1'-18' that were used in the second generation array of Example 2.

The 18 monomers selected from the first generation assay are shown as monomers 1'-18' in FIG. 7.

Figure 8:
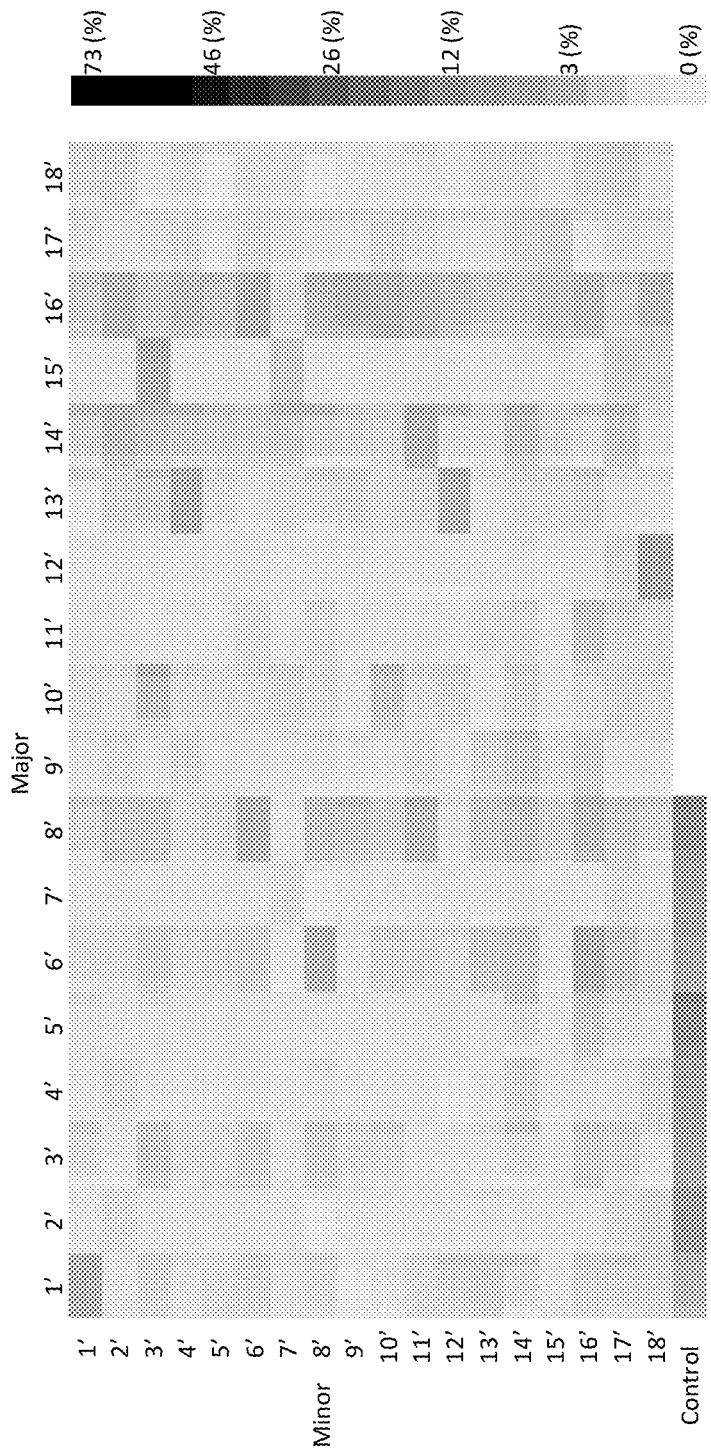
FIG. 8 shows the determined t values for each of the polymers tested in the second generation array of Example 2. The monomers indicated in the x-axis refer to the monomer used as the majority monomer and the monomers indicated in the y-axis refer to the monomer used as the minority monomer. In each case the ratio of majority monomer to minority monomer was 2:1. The intensity scale (note log scale) on the right hand side indicates the numerical value for each polymer, with one polymer represented by each square.

The determined τ values for each of the polymers in this array are shown in FIG. 8.

The monomers indicated in the x-axis refer to the monomer used as the majority monomer and the monomers indicated in the y-axis refer to the monomer used as the minority monomer. In each case the ratio of majority monomer to minority monomer was 2:1.

The intensity scale (note log scale) on the right hand side indicates the numerical value for each polymer, with one polymer represented by each square. For each copolymer three values are shown. The wide column indicates the mean measurement taken for this polymer. The thin column to the direct right of the mean is one standard deviation unit subtracted from the mean and the thin column to the left of the mean is one standard deviation unit added to the mean.

From the screen of the second generation array the top 20 hits were selected.

The bacterial performance (1) values for these compositions are shown in FIG. 9.

The tested compositions also resisted bacterial attachment mediated by the mineralisation of salt components within urine and by non-mineral components within urine, such as creatinine and urea.

Example 3

Figure 10:
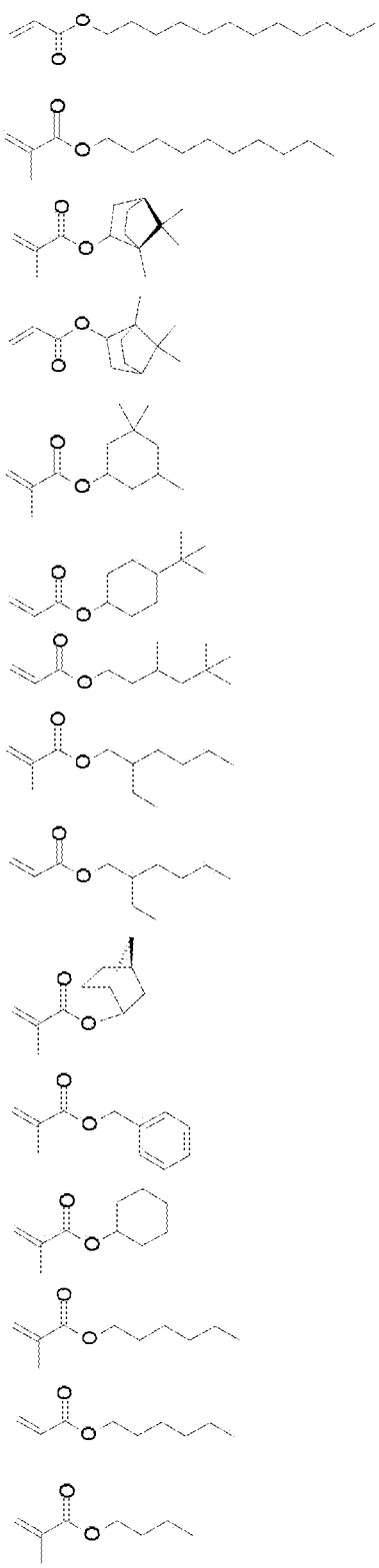
FIG. 10 shows the monomers used in Example 3, where a microarray was produced that contained homopolymers of 15 (meth) acrylate monomers that had aliphatic, cyclic or aromatic pendant groups.

To further investigate the role of amphiphilic materials for preventing bacterial attachment, a microarray was produced that contained homopolymers of 15 (meth) acrylate monomers that had aliphatic, cyclic or aromatic pendant groups. The monomers are shown in FIG. 10.

The biological performance of test materials consisting of homopolymers formed from aliphatic, cyclic and aromatic acrylate and methacrylate monomers was tested in a polymer microarray format. The fluorescence intensity F was measured after 72 h incubation with *P. aeruginosa* (PA), *S. aureus* (SA) and UPEC in RPMI-1640. The bacterial performance (τ) values were also calculated.

Figure 11:
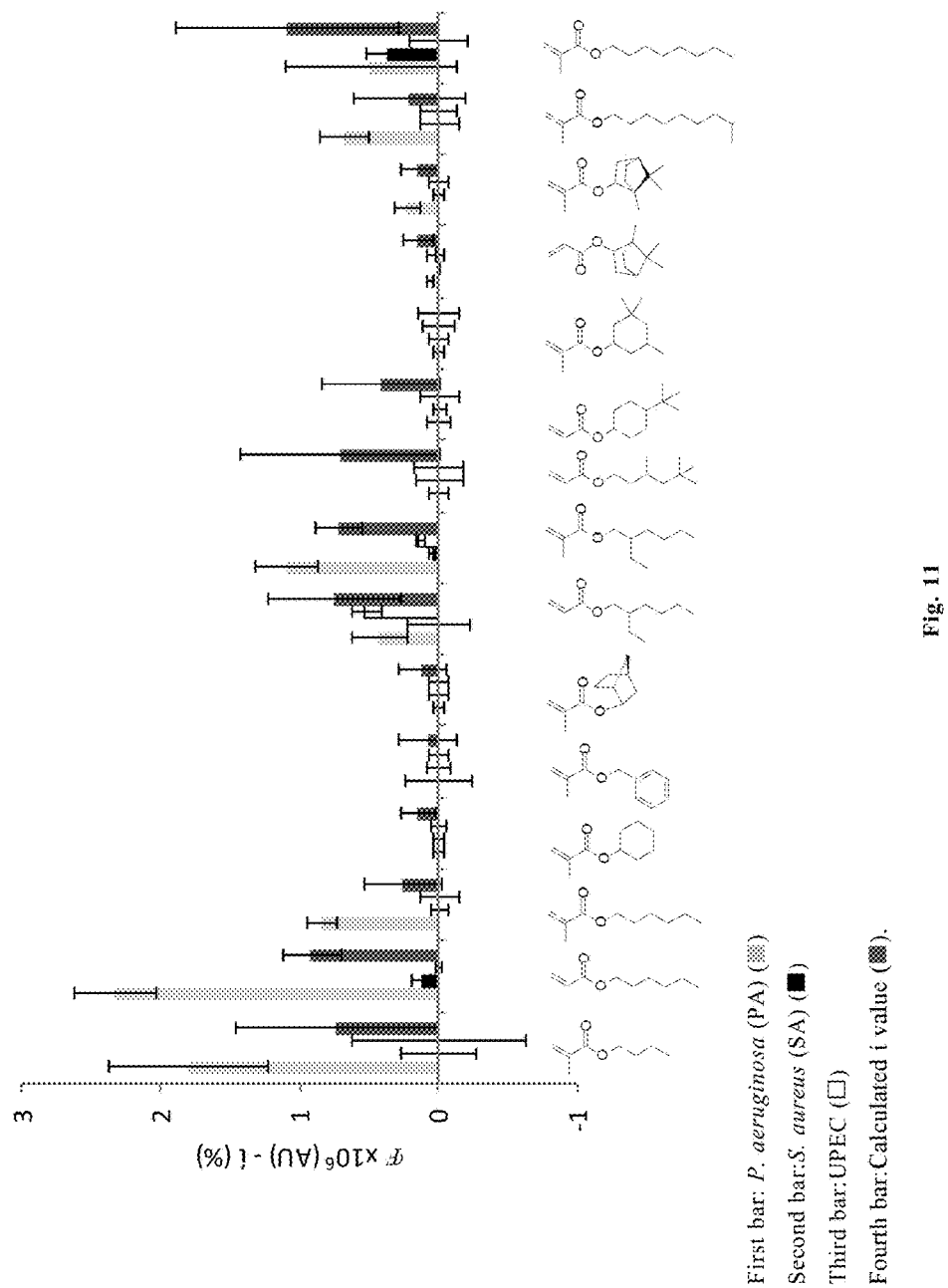
FIG. 11 shows the biological performance of the homopolymers tested in Example 3, with the F values as measured after 72 h incubation with *P. aeruginosa* (PA), *S. aureus* (SA) and UPEC being shown, as well as the calculated i value.

The fluorescence intensity (F) from GFP *P. aeruginosa*, *S. aureus* and UPEC for each material, and the composite bacterial performance assessment (i) of these three intensities, is shown in FIG. 11. The calculated i value is also shown (¢). The chemical structure of the monomer used is shown under the corresponding F and i value and is ranked from left to right by increasing number of carbon atoms. Error bars equal ±one standard deviation unit: n=3.

FIG. 11 therefore shows the biological performance of test materials consisting of homopolymers formed from aliphatic, cyclic and aromatic acrylate and methacrylate monomers on a polymer microarray format. F measured after 72 h incubation with *P. aeruginosa* (PA) ( ), *S. aureus* (SA) (■) and UPEC (□) in RPMI-1640. The calculated i value is also shown ( ).

The relatively high bacterial attachment observed for *P. aeruginosa* provided the greatest distinction between the materials. The materials with the lowest FPA all contained cyclic or aromatic hydrocarbon groups. In contrast, the materials with the highest i all contained only aliphatic carbon pendant groups. This suggests that the presence of ring structures may help reduce or prevent bacterial attachment to acrylate polymers.

For example, comparing hexyl methacrylate ($F_{PA}$=0.85×$10^6$±0.11×$10^6$ AU) with cyclohexyl methacrylate ($F_{PA}$=0.00×$10^6$±0.04×$10^6$ AU) and decyl methacrylate ($F_{PA}$=0.68×$10^6$±0.17×$10^6$ AU) with isobornyl methacrylate ($F_{PA}$=0.22×$10^6$±0.09×$10^6$ AU), both monomers within each pair contain the same number of carbon atoms but in each case a lower bacterial attachment was measured on the material formed from the monomer with the ring structure.

The DNA SYTO17 binding dye used to detect the coverage of bacteria indicated that in general there were neither dead nor live bacteria on the hit materials after 72 h incubation with planktonic bacteria. Thus the mechanism behind the low attachment is anti-adhesive rather than a killing mechanism. Consistent with this, growth curves showed no inhibition by the 'hit' polymers for the bacterial strains used and live/dead staining of the UPEC biofilms that were present on polymer coupons revealed both live and dead cells within the biofilm, which is typical of biofilms.

Furthermore, there was no evidence of cytotoxicity, since the materials under investigation supported the culture of delicate embryonic stem cell lines.

Example 4

In-vivo testing was carried out to assess the extent of clearance of bioluminescent *S. aureus* Xen29 strain (5×105 cells) on a urinary catheter in a mouse infection model (as proposed by Kuklin, 2003). An uncoated catheter was compared with a catheter coated with materials according to the invention. Material was chosen on the basis of the previously assessed performance in inhibiting bacterial attachment in serum free environments (RPMI).

Figure 12:
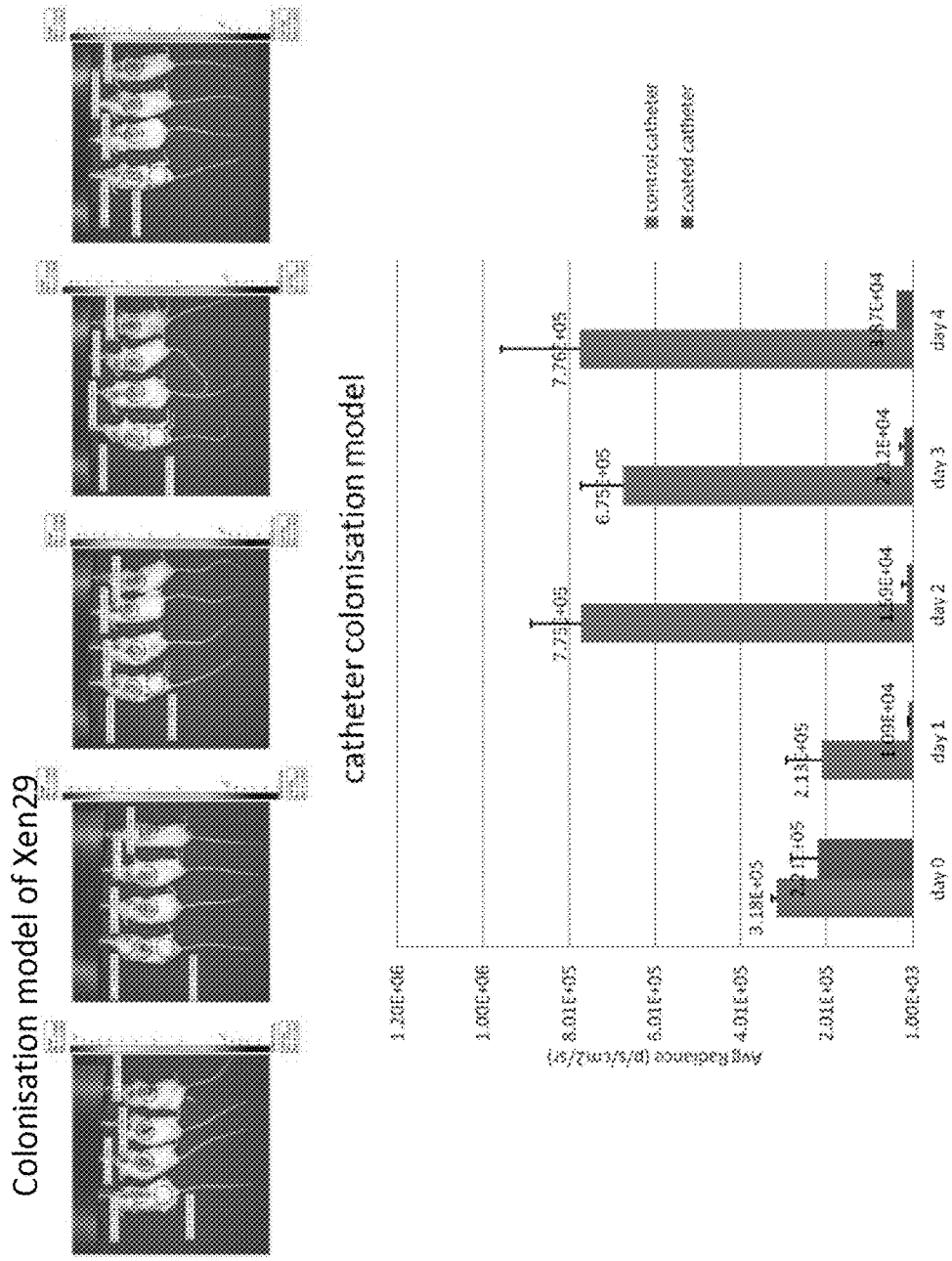
FIG. 12 shows preliminary data from in-vivo testing in Example 4 to assess the extent of clearance of bioluminescent *S. aureus* Xen29 strain (5×105 cells) on a urinary catheter in a mouse infection model. An uncoated catheter was compared with a catheter coated with materials according to the invention.

The preliminary data are shown in FIG. 12. These show a clearance of bioluminescent *S. aureus* Xen29 strain in a mouse infection model. Therefore the effects for the polymers of the invention are repeatable in an in-vivo environment.

In this tissue contacting environment the surface is essentially bathed in a serum ultrafiltrate, which will contain proteins. A superior performance is expected to be achieved on materials designed to resist both protein adsorption and bacterial attachment, since the materials used to date are likely partially compromised in their performance by the protein conditioning layer.

Example 5

Summary

Monomer 4 (as shown in FIG. 1) was catalytically chain-transfer polymerised with DEGMA to lower the polymer's glass transition temperature ($T_g$) to below room temperature, hence improving the polymer's flexibility. The polymer was then coated onto silicone catheters and inserted subcutaneously into mice, where the antibacterial properties of the polymer coating were tested.

Methods

Polymer Formation

Catalytic chain transfer polymerised polymer was prepared by formation of a degassed solution of 15% (v/v) monomer 4 as shown in FIG. 1 (ethylene glycol dicyclopentenenyl ether acrylate), 5% (v/v) di(ethylene glycol) methyl ether methacrylate (DEGMA), 0.5% (w/w) 2,2'-azobis-(2,4-dimethyl-4-methoxyvaleronitrile) and 2000 ppm tetraphenylcobaloxime boron fluoride (bis[(difluoroboryl)diphenylglyoximato]cobalt (II)) in DCM. This polymerisation solution was placed in a Schlenk tube, under vacuum at 35° C. for 24 h with stirring. The vessel was then placed into an icebath for 5 min before decanting.

DEGMA was included in the copolymer mixture to reduce the polymer's $T_g$ and hence increase the polymer's flexibility. This monomer was also included to exploit the ability of the oligo(ethylene glycol) moiety to reduce protein adsorption, which is important for the protein-rich in vivo conditions. For this purpose, DEGMA was selected from a selection of three candidate hydrophilic monomers that were photopolymerised and screened for low bacterial attachment properties according to the methods described in example 1. The results of this study are shown below in Table 1.

TABLE 1

Bacterial attachment screen of hydrophilic monomers. The fluorescence signal measured for each bacterial species on each polymer is provided, including the bacterial performance (i).

| | Pseudomonas aeruginosa ($\times 10^6$) | Staphylococcus aureus ($\times 10^6$) | Uropathogenic Escherichia coli ($\times 10^6$) | i (%) |
|---|---|---|---|---|
| DEGMA | 4.26 | 0.11 | 0.06 | 1.42 |
| Carboxyethyl acrylate | 0.89 | 0.06 | 3.61 | 6.17 |
| Poly (ethylene glycol) methyl ether acrylate | 10.31 | 4.24 | 0.15 | 8.14 |

The resultant polymer was characterised by NMR, GPC and DSC to determine the polymer's composition, molecular weight, polydispersity and $T_g$. These characteristics are shown in Table 2 below.

Nuclear magnetic resonance (NMR) experiments were performed at 298 K. 1H and 13C NMR spectra were acquired on a Bruker DPX300 instrument fitted with a 5 mm autotunable broad-band (BBFO) probe. Differential scanning calorimetry (DSC) measurements were conducted on a DSC Q2000 (TA Instruments). Samples were placed in a Tzero Hermetic Pan with a pressed lid. Heat flow was measured against a sealed empty pan. Each sample was cycled between −40° C. and 90° C. three times at 10° C./min. Number-average molecular weight (Mn), weight-average molecular weight (Mw), and polydispersity (PD) were obtained by gel permeation chromatography (GPC) (PL-120, Polymer Laboratories) with an RI detector. The columns (30 cm PLgel Mixed-C, 2 in series) were eluted by DCM and calibrated with polystyrene standards. All calibrations and analyses were performed at 40° C. and a flow rate of 1 mL/min.

TABLE 2

Characterisation of solution polymerised polymer.

| Monomers | Monomer ratio in polymerisation solution | Measured monomer ratio in polymer by NMR | $M_n$ | $M_w$ | PDI | Tg (° C.) |
|---|---|---|---|---|---|---|
| Monomer 4 and DEGMA | 75/25 | 74/26 | 18000 | 31000 | 1.72 | 9 |

In Vivo Testing

The polymer solution was used to dip-coat an oxygen plasma etched silicone catheter segment. Dip-coated catheters were dried at <50 mTorr for at least 7 days.

To evaluate the in vivo resistance of polymer materials to bacterial attachment, the real time, non-invasive catheter foreign body implant model was used (as proposed by Kuklin, 2003). In this regard, the dip-coated catheters were implanted subcutaneously into mice and inoculated with bioluminescent S. aureus Xen29.

Sterilized (UV) uncoated and coated silicone catheters of 1 cm length were implanted subcutaneously into the flanks of Balb/C mice (4 per group). After 24 h recovery, $1 \times 10^5$ bioluminescent S. aureus Xen29 (Caliper Life Sciences Inc) in 50 μl PBS were injected into the lumen of the catheter.

Bioluminescence was measured at the infection site using an IVIS whole animal imager (Caliper Life Sciences Inc.) and the total photon emission from the catheter were quantified by using the living image software package (Xenogen Corp), over a 4 day period.

At day 4 the mice were sacrificed, the catheter was explanted, the mouse kidneys and spleen were harvested, and the number of bacteria at each site determined.

Specifically, the number of colony forming units (cfu) counts were determined from both the catheter and organs using standard procedures. The cfu counts were normalized to the mass of tissue taken. Reported bioluminescence values have had the background luminescence measured from inserted catheters with no inoculation subtracted.

Results

Figure 13A:
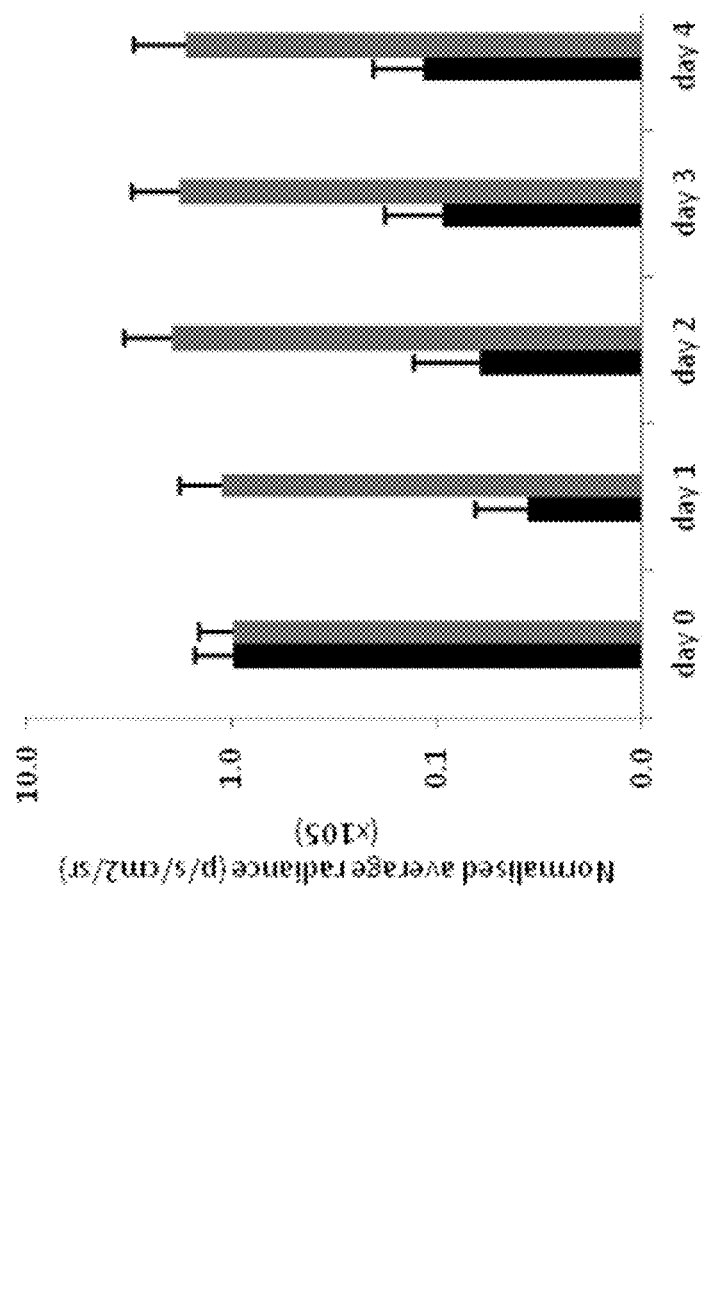
FIG. 13a shows results from Example 5, in relation to the measured bioluminescence at the infection site on the day of inoculation (day 0) and for the next 4 days. Measurements were taken for both coated (left hand bar) and uncoated (right hand bar) silicone catheters. The error bars represent ±one standard deviation unit: n=5. Bioluminescence was normalised to the output at day 0 and all measurements have had the background luminescence subtracted, measured in a mouse with an un-inoculated catheter implant.
Figure 13B:
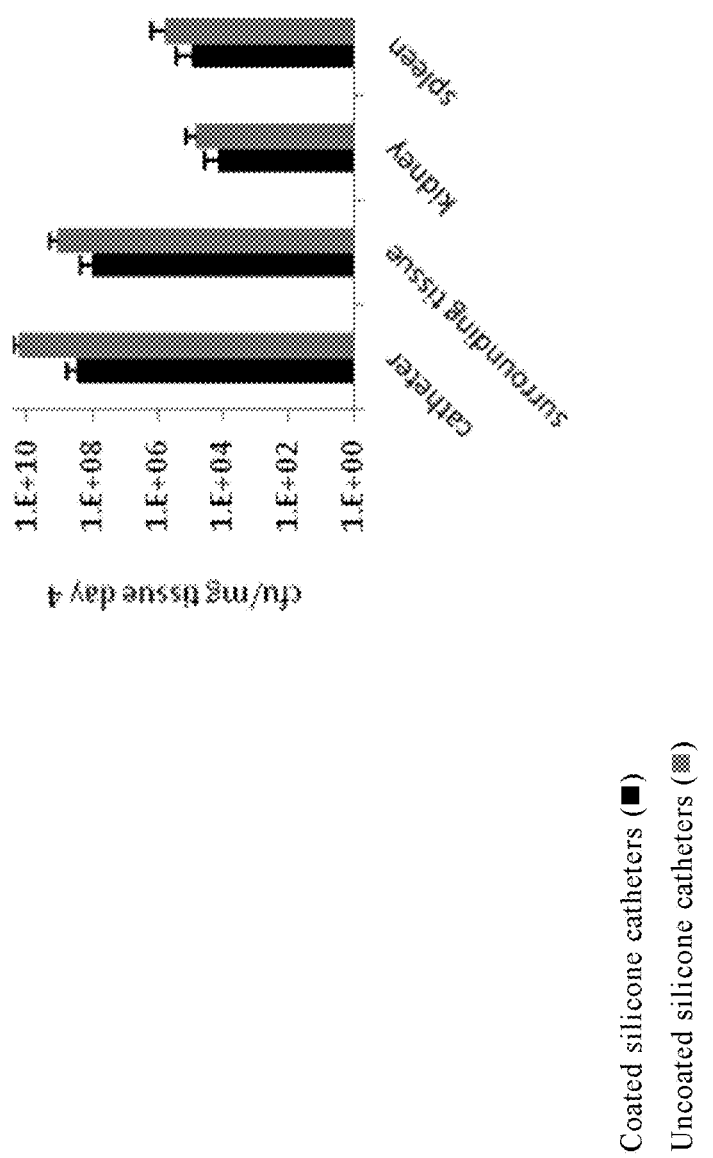
FIG. 13b shows results from Example 5, in relation to the colony forming unit (cfu) counts as determined from the catheter, tissue and organs for both coated (left hand bar) and uncoated (right hand bar) silicone catheters after 4 days from inoculation. The error bars represent ±one standard deviation unit: n=9.

Results are shown in FIGS. 13a and 13b.

FIG. 13a shows the bioluminescence at the infection site as measured on the day of inoculation (day 0) and for the next 4 days. Measurements were taken for both coated (■, left hand bar) and uncoated (▧, right hand bar) silicone catheters. The error bars represent ±one standard deviation unit: n=5. Bioluminescence was normalised to the output at day 0 and all measurements have had the background luminescence subtracted, measured in a mouse with an un-inoculated catheter implant.

FIG. 13b shows colony forming unit (cfu) counts as determined from the catheter, tissue and organs for both coated (■, left hand bar) and uncoated (▧, right hand bar) silicone catheters after 4 days from inoculation. The error bars represent ±one standard deviation unit: n=9.

Immediately following inoculation a high bioluminescence was observed for both coated and uncoated catheters ($1.13 \times 10^5$ p/s/cm²/sr±$0.50 \times 10^5$ p/s/cm²/sr and $2.03 \times 10^5$ p/s/cm²/sr±$1.32 \times 10^5$ p/s/cm²/sr, respectively). After 1 day an order of magnitude reduction in bioluminescence was observed in the coated catheters compared with the uncoated silicone catheters that persisted for 4 day (FIG. 13a). Conversely, bioluminescence remained constant on the silicone catheter, increasing marginally to $2.68 \times 10^5$ p/s/cm²/sr±$2.28 \times 10^5$ p/s/cm²/sr after 4 days.

The reduction of bioluminescence on the coated catheter demonstrates that the coating successfully prevented bacterial attachment to the catheter, facilitating bacterial clearance by host defences. In contrast on the silicone catheter the bacteria were able to attach to the silicone and avoid clearance. Bioluminescence requires the bacteria to be respiring aerobically, however, and so it will not detect bacteria that are viable but are either dormant or growing anerobically.

Thus, to confirm reduced bacterial numbers, the mice were sacrificed on day 4 and bacterial numbers were counted at the infection site (both the catheter and surrounding tissue), kidneys and spleen. Bacterial numbers were seen to be reduced by nearly two orders of magnitude on the coated catheter compared to the uncoated catheter, whilst an order of magnitude reduction in bacterial numbers was observed at the surrounding tissue of the infection site, the kidneys and the spleen (FIG. 13b). This indicates that there was a reduced amount of systemic bacteria when the coating was used.

These results therefore confirm the ability of the polymer coating of the invention to reduce bacterial attachment in vivo.

Example 6

Summary

Thirteen hits out of the second generation array of Example 2 were selected and the monomer ratios for these were then systematically varied to produce a third generation array with 169 unique copolymer materials that allowed the optimisation of the hit compositions. Hits from the third generation array were scaled out to 60 replicates, and also scaled up to 6 mm diameter polymer coupons. The antibacterial properties of the hit compositions were verified in both scaled up and scaled out formats.

Methods

Third Generation Array

Thirteen hits with low i were selected out of the second generation array of Example 2 for use in a third generation array. The focus of this array was to optimise the composition of the material. Thus, each hit composition had the ratios of its monomers systematically varied, with ratios of 1:0, 9:1, 4:1, 3:1, 2:1, 1:1, 1:2, 1:3, 1:4, 1:9 and 0:1 being tested. Three positive controls were also included in this array.

The array was incubated with *P. aeruginosa*, *S. aureus* and UPEC for 72 hours and i was determined for each material. From the third generation array the top 10 hit formulations were selected for scale out and scale up.

Polymer Scale Out

In the material scale out (i.e. increased number of replicates), 60 replicates of the 10 hit formulations, plus homopolymers of the respective monomers as controls, were printed as an array and screened again for bacterial attachment.

Two positive controls were used in this experiment: the homopolymer of monomer A' (Hydroxy-3-phenoxypropyl acrylate) and the copolymer of monomer C' (Tetra(ethylene glycol)diacrylate) and monomer B' (Dimethylamino-propyl acrylate).

Polymer Scale Up

The 10 hit formulations were also scaled up to 6-10 mm diameter polymer coupons. Polymer coupons were formed by pipetting 6 µL of polymerisation solution onto a pHEMA coated slide and irradiating for 10 minutes at $O_2$<1300 ppm with a long wave UV source. Once formed, the polymers were dried at <50 mTorr for 7 days.

Cell Culture

Polymer coupons were washed in distilled $H_2O$ for 10 minutes and air-dried. UV-sterilized polymer samples were incubated in 15 ml RPMI-1640 defined medium (Sigma, UK) inoculated with diluted ($OD_{600}$=0.01) bacteria from overnight cultures at 37° C. with 60 rpm shaking for 24 hours or 72 hours. Samples in medium without bacteria were also set up for medium control.

After incubation with *P. aeruginosa*, *S. aureus* and UPEC the bacteria were stained with the DNA dye SYTO17 and visualised by confocal microscopy. This enabled the determination of the % coverage of bacteria on the polymer coupons.

Specifically, at the desired time points, the samples were removed from bacterial culture and washed with 15 ml phosphate buffered saline (PBS, Oxoid, UK) at room temperature for 5 minutes three times, then rinsed with distilled $H_2O$ to remove salt and air dried. The samples were then stained with 20 µM SYTO17 dye (Invitrogen, UK) at room temperature for 30 min. After air drying, the samples were examined using a Carl Zeiss LSM 700 Laser Scanning Microscope with ZEN 2009 imaging software (Carl Zeiss, Germany). The coverage of bacteria on the surface was analysed using open source Image J 1.44 software (National Institute of Health, US).

Tissue culture polystyrene (TCPS) was used in this experiment for comparison.

Results

Third Generation Array

Figure 14A:
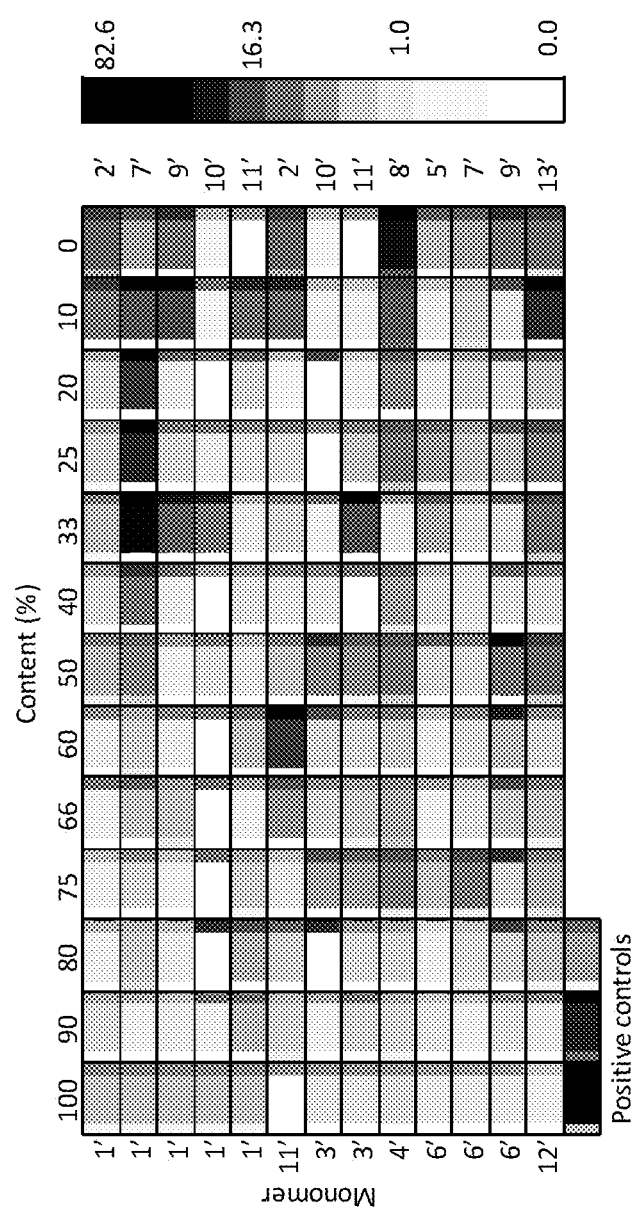
FIG. 14a shows an intensity scale image of i for each of the materials in the third generation array of Example 6. The scale on the right is non-linear, to highlight the range of the array. The monomers used are indicated to the left and right of the intensity scale. The % content of the monomers listed on the left is indicated in the top row. The central square is the i, whilst the narrow columns to the right indicate ±one standard deviation unit, n=4.

The results for the array are shown in FIG. 14a which is an intensity scale image of i for each of the materials in the third generation array, according to the scale given on the right. The scale is non-linear to highlight the range of the array. The monomers used are indicated to the left and right of the intensity scale. The % content of the monomers listed on the left is indicated in the top row. The central square is the i, whilst the narrow columns to the right indicate ±one standard deviation unit, n=4.

Polymer Scale Out

Figure 14B:
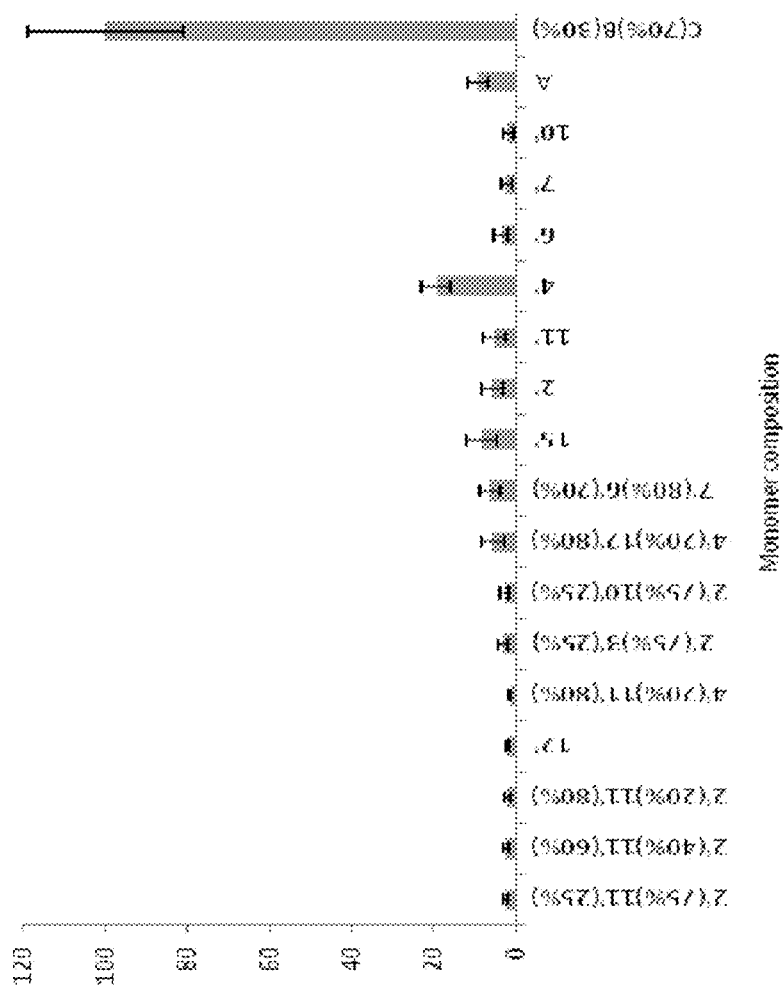
FIG. 14b shows the measured i for the scale out materials tested in Example 6. The error bars equal ±one standard deviation unit, n=60.

The measured i for each material is shown in FIG. 14b. The error bars equal ±one standard deviation unit, n=60.

The i values after scale-out were below the positive controls for all of the tested materials except the homopolymer of monomer 4.

Polymer Scale Up

Figure 14C:
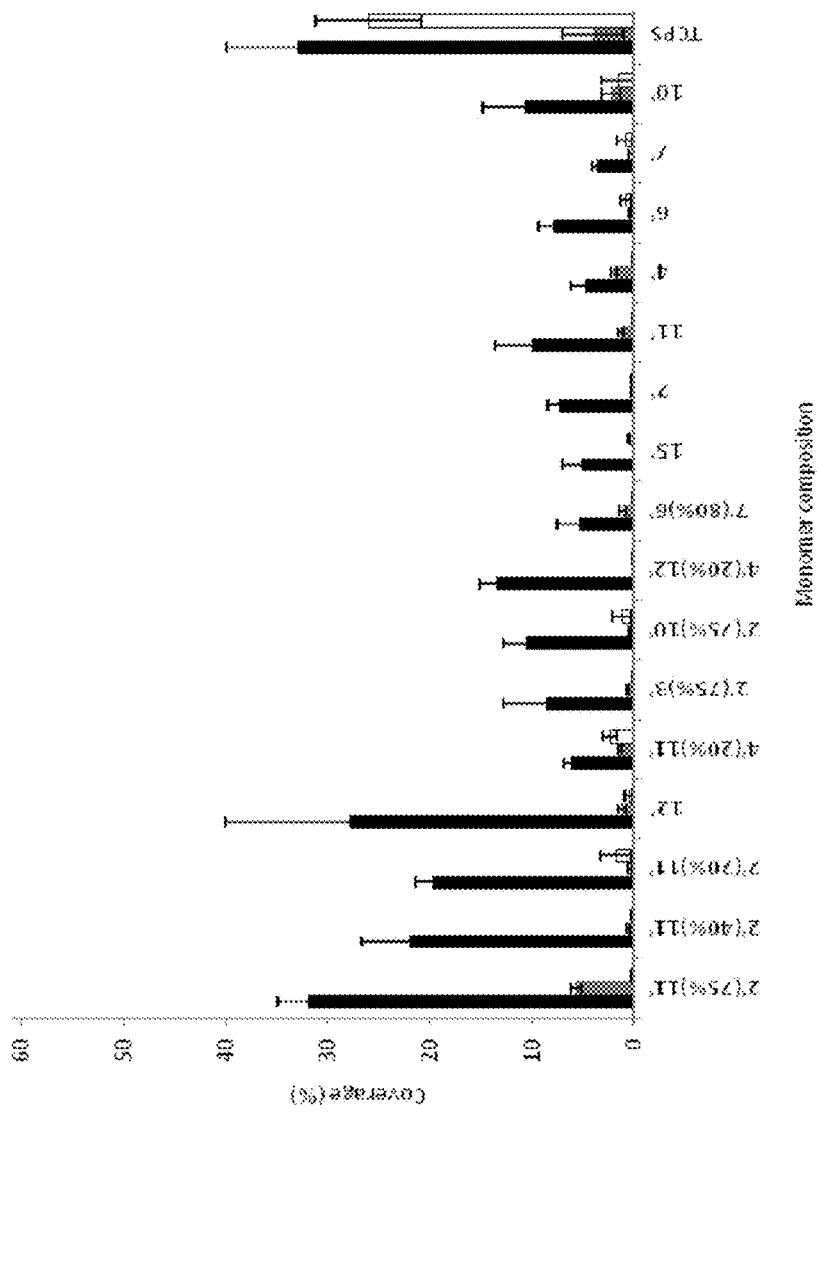
FIG. 14c shows the coverage results on polymer coupons the scale up materials tested in Example 6, in respect of *P. aeruginosa*, *S. aureus*, and UPEC. Error bars equal ±one standard deviation unit, n=3.

The measured coverages are shown for each strain in FIG. 14c, which shows the coverage results in respect of *P. aeruginosa* (■), *S. aureus* (▨), and UPEC (□) on polymer coupons of hit formulations. Error bars equal ±one standard deviation unit, n=3.

A lower bacterial coverage was measured on all hit materials for *P. aeruginosa* and UPEC, and a lower coverage was measured for 15 of the 16 hit materials (including homopolymers) for *S. aureus* compared with TCPS, whilst seven materials had a greater than 70% reduction in bacterial coverage compared with TCPS for all three bacterial species.

The materials that performed best for each species were the homopolymer of monomer 7', which had a *P. aeruginosa* coverage of 3.68%±0.46% (1 standard deviation unit, n=3), the homopolymer of monomer 15', which had a *S. aureus* coverage of 0.13%±0.03%, and the copolymer of monomer 7' (80%, v/v) and monomer 6' (20%, v/v), which had a UPEC coverage of 0.05%±0.02%.

The material with the best broad spectrum performance was the homopolymer of monomer 15', which had a bacterial coverage for *P. aeruginosa*, *S. aureus* and UPEC of 5.09%±1.91%, 0.13%±0.03% and 0.52%±0.12%, respectively.

GENERAL CONCLUSION

Monomers containing hydrophobic moieties such as aromatic and aliphatic carbon groups, when accompanied by the weakly polar ester groups of a (meth) acrylate or (meth) acrylamide, have been identified for use in forming polymers that serve to prevent or reduce bacterial attachment, especially in a urinary catheter environment. By comparison with polystyrene (a purely hydrophobic material that supports bacterial attachment) the weakly amphiphilic structure of these polymers appears to be important in the attachment prevention mechanism.

Figure 15:
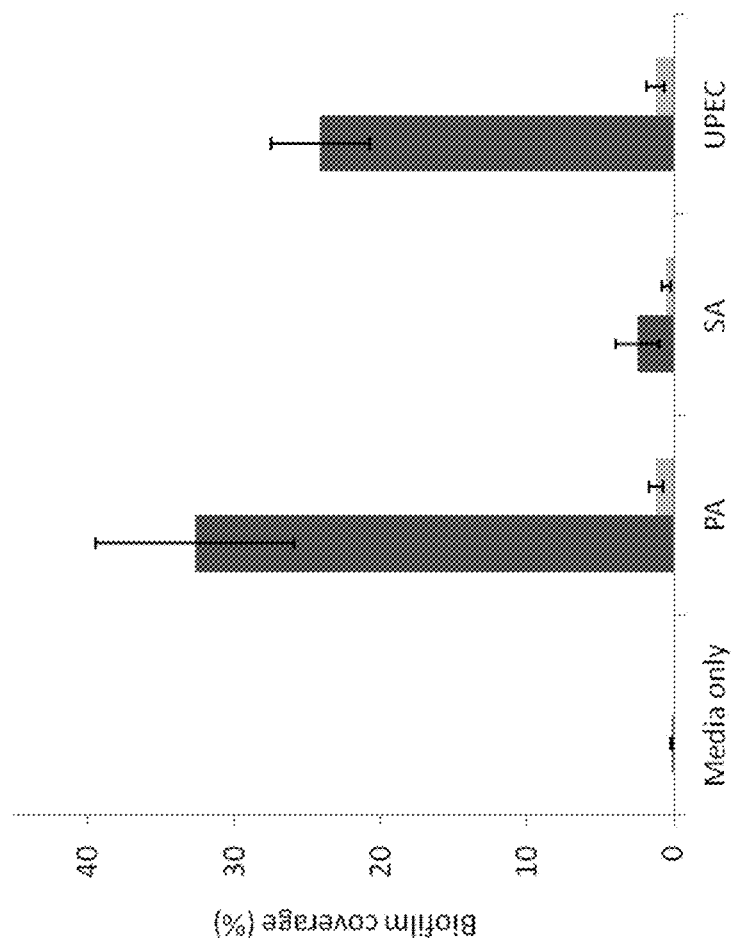
FIG. 15 shows biofilm coverage as measured on poly (styrene) (left hand bars) and on compositions of the invention (right hand bars) for each bacterial strain after 72 h incubation with *P. aeruginosa* (PA), *S. aureus* (SA) and UPEC in RPMI-1640.

A comparison is shown in FIG. 15. This shows biofilm coverage measured on poly(styrene) (■) (left hand bars) and the respective inventive compositions ( ) (right hand bars) for each bacterial strain after 72 h incubation with *P. aeruginosa* (PA), *S. aureus* (SA) and UPEC in RPMI-1640.

It can be seen that poly(styrene) (left hand columns) is significantly less successful than the inventive compositions (right hand columns) in preventing bacterial attachment for each bacterial strain (*P. aeruginosa* (PA), *S. aureus* (SA) and UPEC) after 72 h incubation.

The ability of polymers formed from the (meth) acrylate/ (meth) acrylamide monomers to resist the attachment of bacteria with very different macromolecular surface compositions is likely to be related to the ability of bacterial cells to sense and respond to their immediate environment. This may be a consequence of the individual cells or the bacterial population collectively sensing the nature of the polymer surface via cell envelope associated sensory proteins and through quorum sensing (bacterial cell-to-cell communication) mechanisms, such that the lack of bacterial attachment occurs through these decision making processes rather than simply being a consequence of physico-chemical interactions between the bacteria and surface alone. An example of this is the Rcs sensor kinase which controls the expression of a number of *E. coli* genes in response to growth on a solid surface. Concomitantly, bacteria are capable of different types of near-surface movement utilizing flagella and type IV pili. Bacterial surface-associated adhesions also play important roles for attachment on solid surfaces. LapA, a secreted protein for *P. fluorescens* permanent attachment, is inhibited by RapA which degrades the second messenger cyclic diguanylate monophosphate (c-di-GMP). The intracellular level of c-di-GMP in *P. seruginosa* also affects the psI and pel gene expressions which are responsive to polysaccharides production. Polysaccharides produced by bacteria contribute to the cell-cell adhesion or cell-surface attachment for further biofilm formation. One of the common exo-polysaccharides is the polymer of b-1,6-N-acetyl-D-glucosamine (PNAG) synthesized and transported by icaADBC loci in staphylococcal species. Three transcriptional regulators, SarX, Rbf and IcaR have been shown their roles on icaADBC loci regulation. SarX also involves in the *S. aureus* Agr quorum sensing system. Thus, it is likely that the bacterial response to a surface is more sophisticated than currently appreciated.

The invention claimed is:

1. An article having a surface comprising a polymer or having a polymer coating, wherein the polymer is a homopolymer formed from a methacrylate, acrylate, acrylamide or methacrylamide monomer or a copolymer formed from one or more methacrylate, acrylate, acrylamide or methacrylamide monomers, wherein the monomers are of formula (I) or (II):

(I)

(II)

wherein
n is 1, 2 or 3,
R' is independently H or CH$_3$,
R is an organic group having a total of from 2 to 24 carbon atoms, wherein the organic group includes an aliphatic or aromatic hydrocarbon moiety and wherein the organic group does not include any hydroxyl groups;
wherein the polymer is formed from at least one monomer of formula (4):

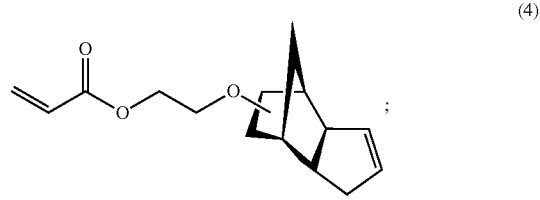

(4)

wherein said article is a medical device selected from the group consisting of surgical instruments, permanent implants, and non-permanent implants.

2. The article of claim 1, wherein the medical device is selected from the group consisting of:
(a) surgical instruments, wherein the surgical instruments are selected from the group consisting of forceps, reamers, pushers, pliers, and retractors;
(b) permanent implants, wherein the permanent implants are selected from the group consisting of artificial heart valves, voice prostheses, prosthetic joints, implanted artificial lenses, stents, and shunts; and
(c) non-permanent implants, wherein the non-permanent implants are selected from the group consisting of pacemakers and pacemaker leads, drain tubes, endotracheal or gastrointestinal tubes, temporary or trial prosthetic joints, surgical pins, guidewires, surgical staples, cannulas, contact lenses, subcutaneous or transcutaneous ports, and indwelling catheters and catheter connectors.

3. The article of claim 1, wherein the polymer is selected from the group consisting of homopolymers formed from monomers of formula (4); and copolymers where 70 wt % or more of the monomers used to form the copolymer are of formula (I) or (II); and mixtures thereof and wherein the copolymer is formed from at least one monomer of formula (4).

4. The article of claim 1 wherein the polymer is selected from the group consisting of homopolymers formed from monomers of formula (4); and copolymers wherein in addition to the monomer of formula (4) some or all of the monomers used to form the copolymer are monomers of formula (I) or (II) where R is an organic group that has a total of from 2 to 24 carbon atoms and that only includes moieties selected from: alkyl, alkenyl, carbonyl, ether, ester, phenyl, cycloalkyl, cycloalkenyl and heterocycloalkyl moieties, each of which may optionally be halogenated.

5. The article of claim 1, wherein the polymer is selected from the group consisting of homopolymers formed from monomers of formula (4); and copolymers wherein in addition to the monomer of formula (4) some or all of the monomers used to form the copolymer are monomers of formula (I) or (II) where R is an organic group that has a total of from 2 to 24 carbon atoms and that includes an aliphatic hydrocarbon moiety which is a C1-C16 straight or branched chain alkyl moiety, or a C5-C16 cycloalkyl moiety or a C5-C16 cycloalkenyl moiety.

6. The article of claim 1 wherein the polymer is selected from the group consisting of homopolymers formed from monomers of formula (4); and copolymers wherein in addition to the monomer of formula (4) some or all of the monomers used to form the copolymer are monomers of formula (I) or (II) where R is an organic group that has a total of from 2 to 24 carbon atoms and that includes moieties selected from: cyclic and aromatic moieties, each of which may optionally be halogenated.

7. The article of claim 1 wherein the polymer is selected from the group consisting of homopolymers formed from monomers of formula (4); and copolymers wherein in addition to the monomer of formula (4) some or all of the monomers used to form the copolymer are monomers of formula (I) or (II) where R is an organic group that has a total of from 2 to 24 carbon atoms and that includes moieties selected from: phenyl, cycloalkyl, cycloalkenyl and heterocycloalkyl moieties, each of which may optionally be halogenated.

8. The article of claim 1 wherein the polymer is selected from the group consisting of homopolymers formed from monomers of formula (4); and copolymers wherein in addition to the monomer of formula (4) some or all of the monomers used to form the copolymer are monomers of formula (I) selected from the group consisting of

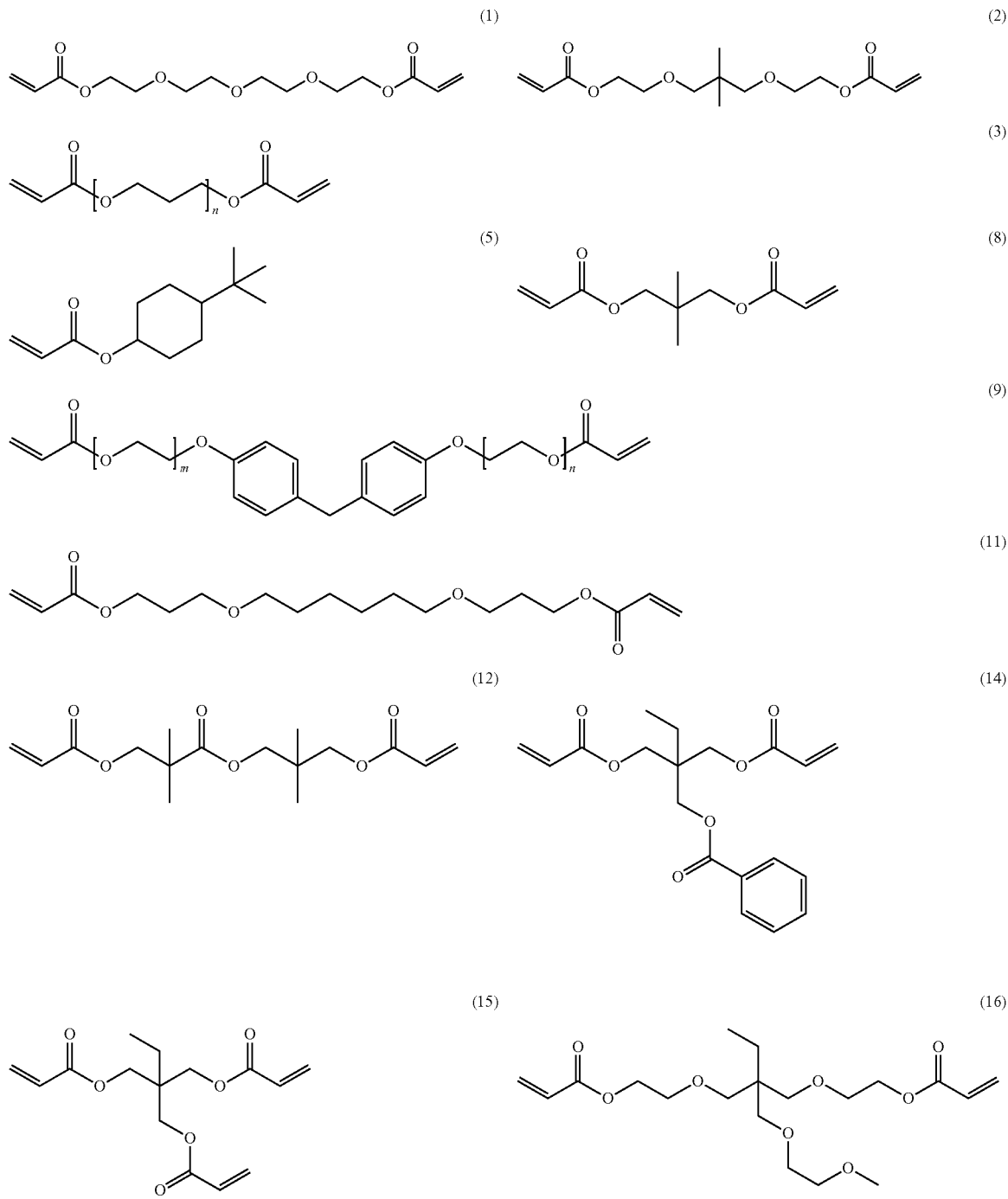

-continued
(B) 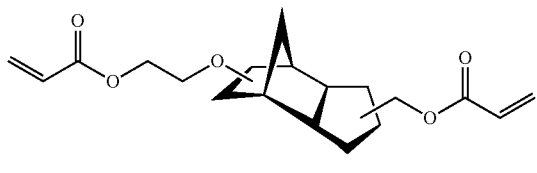
(C) 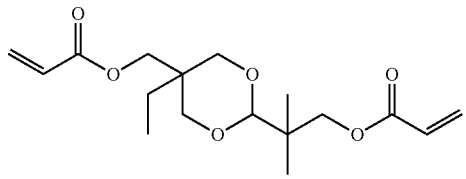
(D) 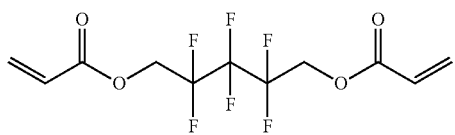
(E) 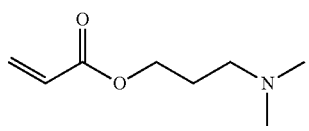
(F) 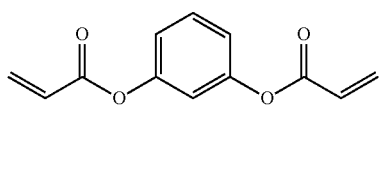
(1') 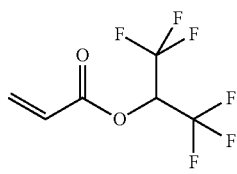
(2') 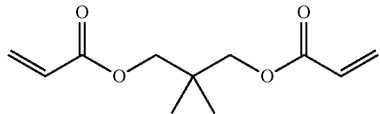
(3') 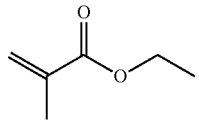
(4') 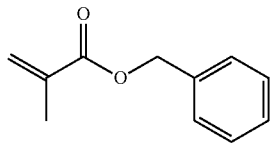
(5') 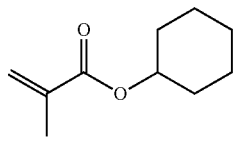
(7') 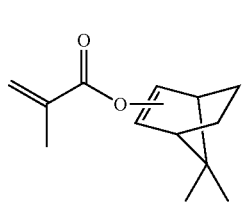
(8') 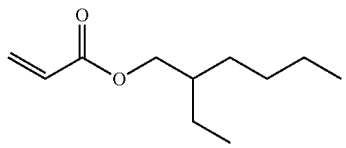
(9') 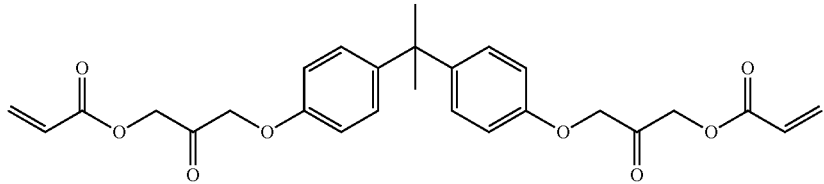
(10') 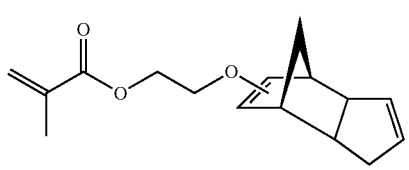
(11') 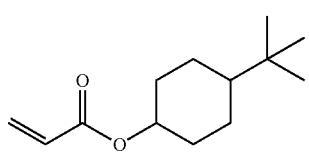

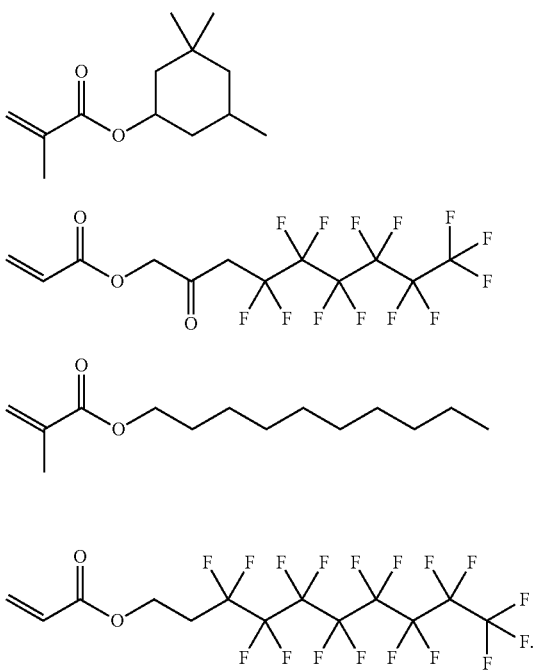
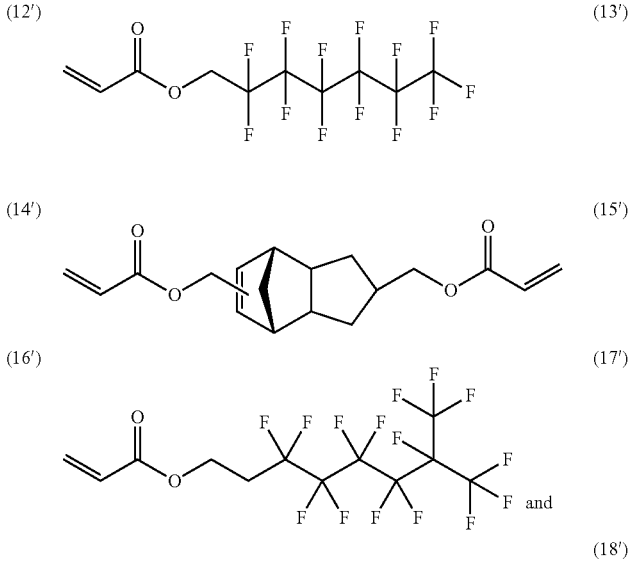
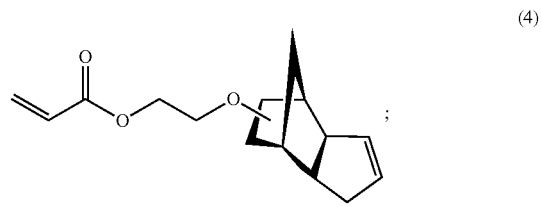

9. The article of claim 8, wherein the polymer is selected from the group consisting of homopolymers formed from monomers of formula (4); and copolymers wherein in addition to the monomer of formula (4) some or all of the monomers used to form the polymer are monomers of formula (I) selected from monomers 5, 8, 15, B, 1', 2', 3', 4', 5', 7', 8', 9', 10', 11', 12', 13', 15', 16' and 18'.

10. The article of claim 9, wherein the polymer is (a) a homopolymer of a monomer of formula (I) selected from monomer 4; or (b) a copolymer wherein 70 wt % or more of the monomers used to form the polymer are selected from monomers 4, 5, 8, 15, B, 1', 2', 3', 4', 5', 6', 7', 8', 9', 10', 11', 12', 13', 15', 16' and 18' and wherein the copolymer is formed from at least one monomer of formula (4).

11. A method for inhibiting bacterial attachment to a surface, or for preventing or reducing biofilm formation by bacteria on a surface, the method comprising:
forming the surface from a polymer, or applying a polymer to the surface,
wherein the polymer is a homopolymer formed from a meth acrylate, acrylate, acrylamide or methacrylamide monomer or a copolymer formed from one or more methacrylate, acrylate, acrylamide or methacrylamide monomers, wherein the monomers are of formula (I) or (II):

[H$_2$C=CR'—C(=O)—O—]$_n$R  (I)

[H$_2$C=CR'—C(=O)—NH—]$_n$R  (II)

wherein
n is 1, 2 or 3,
R' is independently H or CH$_3$,
R is an organic group having a total of from 2 to 24 carbon atoms, wherein the organic group includes an aliphatic or aromatic hydrocarbon moiety and wherein the organic group does not include any hydroxyl groups, wherein the polymer is formed from at least one monomer of formula (4):

(4)

thereby inhibiting bacterial attachment to said surface, or preventing or reducing biofilm formation by bacteria on said surface.

12. The method of claim 11, wherein the bacteria comprise one or more bacteria selected from the group consisting of: *Streptococcus, Staphylococcus, Providencia, Morganella, Stenotrophomonas, Enterococcus, Yersinia, Salmonella, Serratia, Chlamydia, Coxilla, Ehrlichia, Francisella, Legionella, Pasteurella, Brucella, Proteus, Hilicobacter, Klebsiella, Enterobacter, Escherichia, Tropheryma, Acinetobacter, Aeromonas, Alcaligenes, Campylobacter, Capnocytophaga, Bacillus, Clostridium, Corynebacterium, Erysipelothrix, Listeria, Mycobacterium* and *Pseudomonas*.

13. The method of claim 11, wherein the polymer inhibits bacterial attachment mediated by non-mineral components within urine; prevents or reduces biofilm formation mediated by non-mineral components within urine; inhibits bacterial attachment mediated by the mineralisation of salt components within urine; or prevents or reduces biofilm formation mediated by the mineralisation of salt components within urine; or combinations thereof.

14. The method of claim 13, wherein the non-mineral components are selected from the group consisting of creatinine and urea.

15. The method of claim 11, wherein the polymer is selected from the group consisting of homopolymers formed from monomers of formula (4); and copolymers where 70 wt % or more of the monomers used to form the copolymer are of formula (I) or (II); and mixtures thereof, and wherein the copolymer is formed from at least one monomer of formula (4).

16. The method of claim 11 wherein the polymer is selected from the group consisting of homopolymers formed from monomers of formula (4); and copolymers wherein in addition to the monomer of formula (4) some or all of the monomers used to form the copolymer are monomers of formula (I) or (II) where R is an organic group that has a total of from 2 to 24 carbon atoms and that only includes moieties selected from: alkyl, alkenyl, carbonyl, ether, ester, phenyl, cycloalkyl, cycloalkenyl and heterocycloalkyl moieties, each of which may optionally be halogenated.

17. The method of claim 11, wherein the polymer is selected from the group consisting of homopolymers formed from monomers of formula (4); and copolymers wherein in addition to the monomer of formula (4) some or all of the monomers used to form the copolymer are monomers of formula (I) or (II) where R is an organic group that has a total of from 2 to 24 carbon atoms and that includes an aliphatic hydrocarbon moiety which is a C1-C16 straight or branched chain alkyl moiety, or a C5-C16 cycloalkyl moiety or a C5-C16 cycloalkenyl moiety.

18. The method of claim 11 wherein the polymer is selected from the group consisting of homopolymers formed from monomers of formula (4); and copolymers wherein in addition to the monomer of formula (4) some or all of the monomers used to form the copolymer are monomers of formula (I) or (II) where R is an organic group that has a total of from 2 to 24 carbon atoms and that includes moieties selected from: cyclic and aromatic moieties, each of which may optionally be halogenated.

19. The method of claim 11, wherein the polymer is selected from the group consisting of homopolymers formed from monomers of formula (4); and copolymers wherein in addition to the monomer of formula (4) some or all of the monomers used to form the copolymer are monomers of formula (I) or (II) where R is an organic group that has a total of from 2 to 24 carbon atoms and that includes moieties selected from: phenyl, cycloalkyl, cycloalkenyl and heterocycloalkyl moieties, each of which may optionally be halogenated.

20. The method of claim 11, wherein the polymer is selected from the group consisting of homopolymers formed from monomers of formula (4); and copolymers wherein in addition to the monomer of formula (4) some or all of the monomers used to form the polymer are monomers of formula (I) selected from the group consisting of

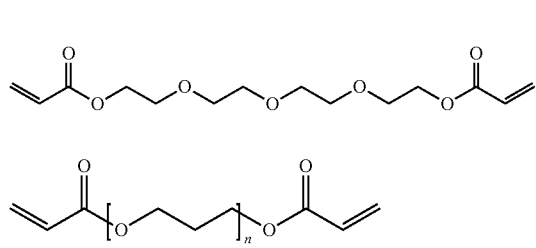

(1)

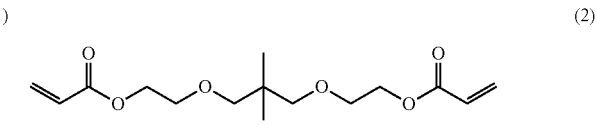

(2)

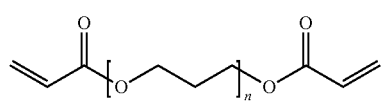

(3)

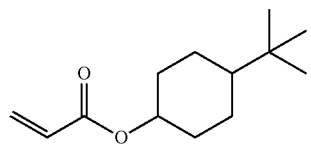

(5)

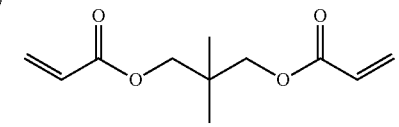

(8)

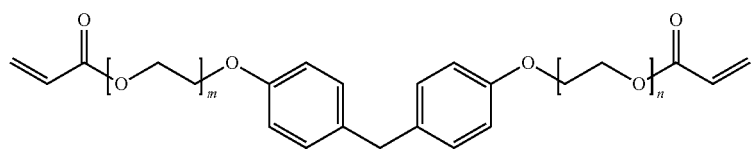

(9)

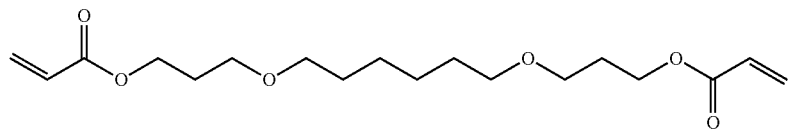

(11)

-continued
(12)
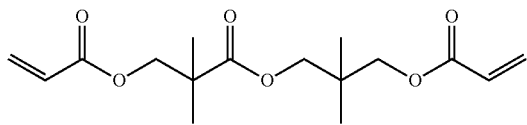
(14)
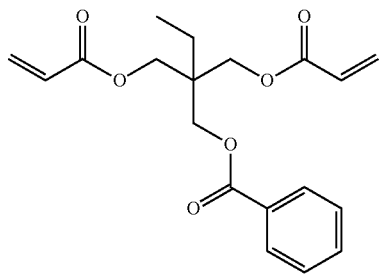
(15)
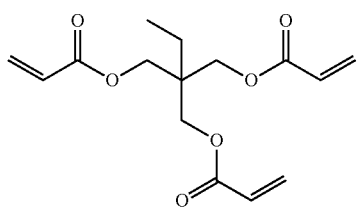
(16)
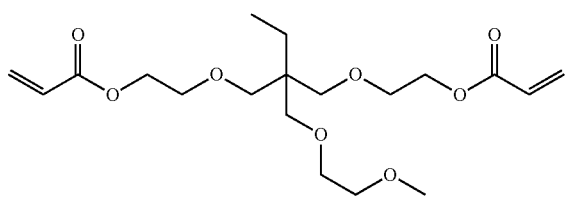
(B)
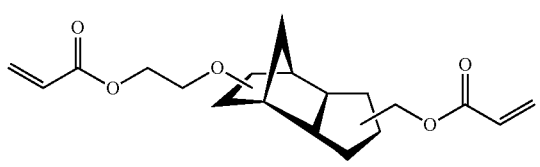
(C)
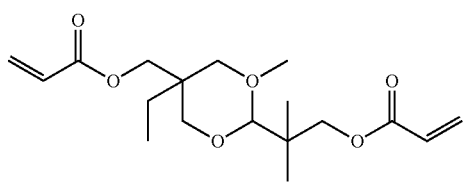
(D)
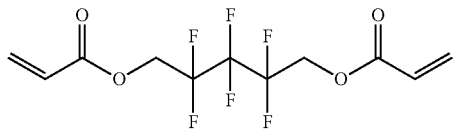
(E)
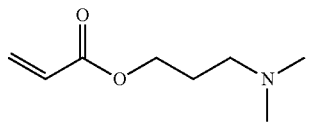
(F)
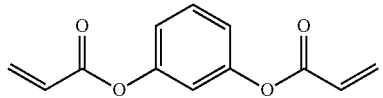
(1')
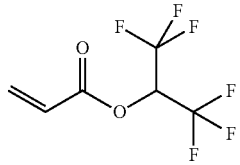
(2')
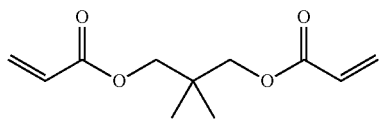
(3')
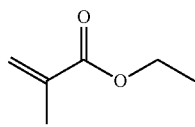
(4')
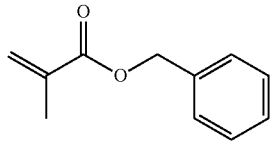
(5')
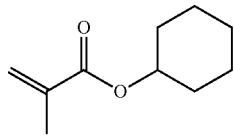
(7')
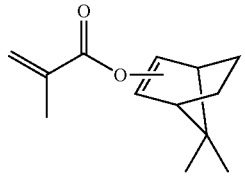

-continued

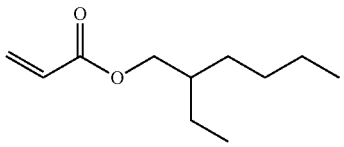
(8')

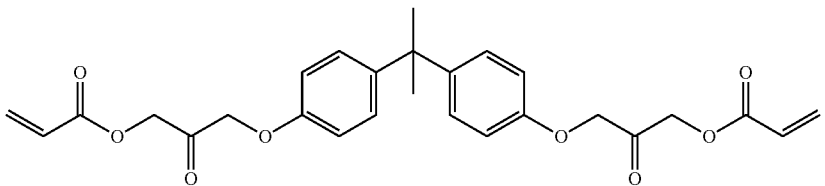
(9')

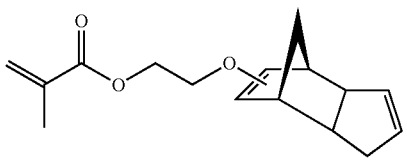
(10')

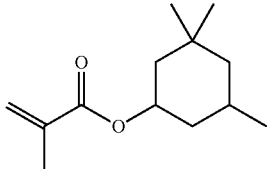
(11')

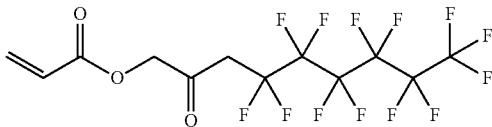
(12')

(13')

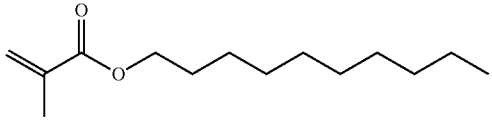
(14')

(15')

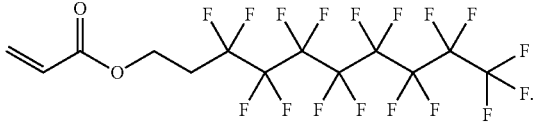
(16')

(17')

and (18')

21. The method of claim 20, wherein the polymer is selected from the group consisting of homopolymers formed from monomers of formula (4); and copolymers wherein in addition to the monomer of formula (4) some or all of the monomers used to form the polymer are monomers of formula (I) selected from monomers 5, 8, 15, B, 1', 2', 3', 4', 5', 7', 8', 9', 10', 11', 12', 13', 15', 16' and 18'.

22. The method of claim 21, wherein the polymer is (a) a homopolymer of a monomer of formula (I) selected from monomer 4; or (b) a copolymer wherein 70 wt % or more of the monomers used to form the copolymer are selected from monomers 4, 5, 8, 15, B, 1', 2', 3', 4', 5', 6', 7', 8', 9', 10', 11', 12', 13', 15', 16' and 18' and wherein the copolymer is formed from at least one monomer of formula (4).

23. The article of claim 1, wherein the polymer is a copolymer,
wherein all of the monomers used to form the polymer are monomers of formula (I),
wherein 70 wt % or more of the monomers used to form the polymer are selected from monomers 4, 5, 8, 15 and monomers 1', 2', 3', 4', 5', 6', 7', 8', 9', 10', 11', 12', 13', 15', 16' and 18', and wherein the polymer is formed from at least one monomer of formula (4):
and wherein a further monomer of formula (I) is used to form the copolymer and is used in an amount of 30 wt % or less and is selected from the group consisting of: di(ethylene glycol) methyl ether methacrylate, ethylene glycol methyl ether methacrylate, ethylene glycol methyl ether acrylate and di(ethylene glycol) ethyl ether acrylate.

24. The method of claim 11, wherein the polymer is a copolymer,
wherein all of the monomers used to form the polymer are monomers of formula (I),
wherein 70 wt % or more of the monomers used to form the polymer are selected from monomers 4, 5, 8, 15 and monomers 1', 2', 3', 4', 5', 6', 7', 8', 9', 10', 11', 12', 13', 15', 16' and 18', and wherein the polymer is formed from at least one monomer of formula (4):

and wherein a further monomer of formula (I) is used to form the copolymer and is used in an amount of 30 wt % or less and is selected from the group consisting of: di(ethylene glycol) methyl ether methacrylate, ethylene glycol methyl ether methacrylate, ethylene glycol methyl ether acrylate and di(ethylene glycol) ethyl ether acrylate.

* * * * *